(12) United States Patent
Alizoti et al.

(10) Patent No.: US 10,786,638 B2
(45) Date of Patent: Sep. 29, 2020

(54) NEBULIZER APPARATUS AND METHOD

(71) Applicant: Trudell Medical International, London (CA)

(72) Inventors: Neritan Alizoti, London (CA); Andrew Dittmer, Woodstock (CA); Luke Kilroy, London (CA); Robert Morton, London (CA); Jennifer Pevler, London (CA); James N. Schmidt, London (CA)

(73) Assignee: Trudell Medical International, London, Ontario (CA)

( * ) Notice: Subject to any disclaimer, the term of this patent is extended or adjusted under 35 U.S.C. 154(b) by 357 days.

(21) Appl. No.: 15/644,427

(22) Filed: Jul. 7, 2017

(65) Prior Publication Data

US 2018/0008789 A1      Jan. 11, 2018

Related U.S. Application Data

(60) Provisional application No. 62/360,165, filed on Jul. 8, 2016.

(51) Int. Cl.
| | | |
|---|---|---|
| *A61M 15/00* | (2006.01) | |
| *A61M 16/14* | (2006.01) | |
| *A61M 16/20* | (2006.01) | |

(52) U.S. Cl.
CPC ...... *A61M 15/0093* (2014.02); *A61M 15/002* (2014.02); *A61M 15/0016* (2014.02); *A61M 15/0018* (2014.02); *A61M 16/14* (2013.01); *A61M 16/208* (2013.01); *A61M 2202/064* (2013.01)

(58) Field of Classification Search
CPC .......... A61M 15/0093; A61M 15/0016; A61M 15/0015; A61M 15/0013
See application file for complete search history.

(56) References Cited

U.S. PATENT DOCUMENTS

| 1,742,740 A | 1/1930 | Watters |
|---|---|---|
| 2,535,844 A | 12/1950 | Emerson |

(Continued)

FOREIGN PATENT DOCUMENTS

| AU | 29969/89 | 8/1990 |
|---|---|---|
| DE | 2804852 A1 | 8/1978 |

(Continued)

OTHER PUBLICATIONS

Product information excerpt, Boehringer Ingelheim, from web address: http://www.torpex.com/product_information/, Aug. 11, 2003 (4 pages).

(Continued)

*Primary Examiner* — Kendra D Carter
*Assistant Examiner* — Suraj Kandalam
(74) *Attorney, Agent, or Firm* — Brinks Gilson & Lione

(57) ABSTRACT

An apparatus and method for providing a nebula or aerosol to a patient is described. In one aspect, the nebulizer is composed of a minimum number of parts to reduce complexity for automated or human assembly. The nebulizer may include an inhalation valve, exhalation valve and biasing member integrated into a single diaphragm structure that may be connected with an actuator and inserted into a housing for controlling nebulization of a medicine to a patient in response to the patient's breathing or in a continuous nebulization mode.

18 Claims, 33 Drawing Sheets

(56) References Cited

U.S. PATENT DOCUMENTS

| | | | |
|---|---|---|---|
| 2,882,026 A | 4/1959 | Eichelman | |
| 2,951,644 A | 9/1960 | Mahon et al. | |
| 3,001,524 A | 9/1961 | Maison et al. | |
| 3,172,406 A | 3/1965 | Bird et al. | |
| 3,269,665 A | 8/1966 | Cheney | |
| 3,467,092 A | 9/1969 | Bird et al. | |
| 3,490,697 A | 1/1970 | Best, Jr. | |
| 3,580,249 A | 5/1971 | Takaoka | |
| 3,584,621 A | 6/1971 | Bird et al. | |
| 3,630,196 A | 12/1971 | Bird et al. | |
| 3,658,059 A | 4/1972 | Steil | |
| 3,664,337 A | 5/1972 | Lindsey et al. | |
| 3,826,255 A | 7/1974 | Havstad et al. | |
| 3,838,686 A | 10/1974 | Szekely | |
| 3,874,379 A | 4/1975 | Enfield et al. | |
| 3,903,884 A | 9/1975 | Huston et al. | |
| 3,990,442 A | 11/1976 | Patneau | |
| 4,093,124 A | 6/1978 | Morane et al. | |
| 4,094,317 A | 6/1978 | Wasnich | |
| 4,106,503 A | 8/1978 | Rosenthal et al. | |
| 4,116,387 A | 9/1978 | Kremer, Jr. et al. | |
| 4,139,128 A | 2/1979 | Ewald | |
| 4,150,071 A | 4/1979 | Pecina | |
| 4,181,151 A * | 1/1980 | Ensign | F16K 7/17 137/625.28 |
| 4,183,361 A | 1/1980 | Russo | |
| 4,198,969 A | 4/1980 | Virag | |
| 4,206,644 A | 6/1980 | Platt | |
| 4,210,140 A | 7/1980 | James et al. | |
| 4,210,155 A | 7/1980 | Grimes | |
| 4,251,033 A | 2/1981 | Rich et al. | |
| 4,253,468 A | 3/1981 | Lehmbeck | |
| 4,268,460 A | 5/1981 | Boiarski et al. | |
| 4,291,688 A | 9/1981 | Kistler | |
| 4,333,450 A | 6/1982 | Lester | |
| 4,413,784 A | 11/1983 | Dea | |
| 4,452,239 A | 6/1984 | Malem | |
| 4,456,179 A | 6/1984 | Kremer | |
| 4,470,412 A | 9/1984 | Nowacki et al. | |
| 4,484,577 A | 11/1984 | Sackner et al. | |
| 4,508,118 A | 4/1985 | Toth | |
| 4,509,688 A | 4/1985 | Gagne et al. | |
| 4,588,129 A | 5/1986 | Shanks | |
| 4,620,670 A | 11/1986 | Hughes | |
| 4,622,968 A | 11/1986 | Persson | |
| 4,627,432 A | 12/1986 | Newell et al. | |
| 4,649,911 A | 3/1987 | Knight | |
| 4,657,007 A | 4/1987 | Carlin et al. | |
| 4,674,491 A | 6/1987 | Brugger et al. | |
| 4,677,975 A | 7/1987 | Edgar et al. | |
| 4,746,067 A | 5/1988 | Svoboda | |
| 4,758,224 A | 7/1988 | Siposs | |
| 4,792,097 A | 12/1988 | Kremer, Jr. et al. | |
| 4,809,692 A | 3/1989 | Nowacki et al. | |
| 4,832,015 A | 5/1989 | Nowacki et al. | |
| 4,911,157 A | 3/1990 | Miller | |
| 4,951,659 A | 8/1990 | Weiler et al. | |
| 4,984,158 A | 1/1991 | Hillsman | |
| 5,012,803 A | 5/1991 | Foley et al. | |
| 5,012,804 A | 5/1991 | Foley et al. | |
| 5,020,527 A | 6/1991 | Dessertine | |
| 5,020,530 A | 6/1991 | Miller | |
| 5,042,467 A | 8/1991 | Foley | |
| 5,054,477 A | 10/1991 | Terada et al. | |
| 5,054,478 A | 10/1991 | Grychowski et al. | |
| 5,078,131 A | 1/1992 | Foley | |
| 5,086,765 A | 2/1992 | Levine | |
| 5,165,392 A | 11/1992 | Small | |
| 5,167,506 A | 12/1992 | Kilis et al. | |
| 5,170,782 A | 12/1992 | Kocinski | |
| 5,209,225 A | 5/1993 | Glenn | |
| 5,235,969 A | 8/1993 | Bellm | |
| 5,241,954 A | 9/1993 | Glenn | |
| 5,277,175 A | 1/1994 | Riggs et al. | |
| 5,280,784 A | 1/1994 | Kohler | |
| 5,299,565 A | 4/1994 | Brown | |
| 5,301,662 A | 4/1994 | Bagwell et al. | |
| 5,301,663 A | 4/1994 | Small, Jr. | |
| 5,309,900 A | 5/1994 | Knoch et al. | |
| 5,312,046 A | 5/1994 | Knoch et al. | |
| 5,312,281 A | 5/1994 | Takahashi et al. | |
| 5,318,015 A | 6/1994 | Mansson et al. | |
| 5,333,106 A | 7/1994 | Lanpher et al. | |
| 5,337,926 A | 8/1994 | Drobish et al. | |
| 5,349,947 A | 9/1994 | Newhouse et al. | |
| 5,363,842 A | 11/1994 | Mishelevich et al. | |
| 5,383,470 A | 1/1995 | Kolbly | |
| 5,385,140 A | 1/1995 | Smith | |
| 5,392,648 A | 2/1995 | Robertson | |
| 5,398,714 A | 3/1995 | Price | |
| 5,427,089 A | 6/1995 | Kraemer | |
| 5,431,154 A | 7/1995 | Seigel et al. | |
| 5,458,136 A | 10/1995 | Jaser et al. | |
| 5,461,695 A | 10/1995 | Knoch | |
| 5,479,920 A | 1/1996 | Piper et al. | |
| 5,487,378 A | 1/1996 | Robertson et al. | |
| 5,497,765 A | 3/1996 | Praud et al. | |
| 5,503,139 A | 4/1996 | McMahon et al. | |
| 5,505,192 A | 4/1996 | Samiotes et al. | |
| 5,505,193 A | 4/1996 | Ballini et al. | |
| 5,511,538 A | 4/1996 | Haber et al. | |
| 5,511,539 A | 4/1996 | Lien | |
| 5,515,842 A | 5/1996 | Ramseyer et al. | |
| 5,520,166 A | 5/1996 | Ritson et al. | |
| 5,522,380 A | 6/1996 | Dwork | |
| 5,533,497 A | 7/1996 | Ryder | |
| 5,533,501 A | 7/1996 | Denyer | |
| 5,544,647 A | 8/1996 | Jewett et al. | |
| 5,549,102 A | 8/1996 | Lintl et al. | |
| 5,570,682 A | 11/1996 | Johnson | |
| 5,582,162 A | 12/1996 | Petersson | |
| 5,584,285 A | 12/1996 | Salter et al. | |
| 5,598,839 A | 2/1997 | Niles et al. | |
| 5,601,117 A * | 2/1997 | Lewis | B60H 1/249 137/527.8 |
| 5,613,489 A | 3/1997 | Miller et al. | |
| 5,617,844 A | 4/1997 | King | |
| 5,622,162 A | 4/1997 | Johansson et al. | |
| 5,630,409 A | 5/1997 | Bono et al. | |
| 5,645,049 A | 7/1997 | Foley et al. | |
| 5,687,912 A | 11/1997 | Denyer | |
| 5,701,886 A | 12/1997 | Ryatt | |
| 5,704,344 A | 1/1998 | Cole | |
| 5,740,793 A | 4/1998 | Hodson et al. | |
| 5,752,505 A | 5/1998 | Ohki et al. | |
| 5,758,638 A | 6/1998 | Kreamer | |
| 5,765,553 A | 6/1998 | Richards et al. | |
| 5,792,057 A | 8/1998 | Rubsamen et al. | |
| 5,803,078 A | 9/1998 | Brauner | |
| 5,816,240 A | 10/1998 | Komesaroff | |
| 5,823,179 A | 10/1998 | Grychowski et al. | |
| 5,848,588 A | 12/1998 | Foley et al. | |
| 5,865,172 A | 2/1999 | Butler et al. | |
| 5,875,774 A | 3/1999 | Clementi et al. | |
| 5,881,718 A | 3/1999 | Mortensen et al. | |
| 5,899,201 A | 5/1999 | Schultz et al. | |
| 5,937,852 A | 8/1999 | Butler et al. | |
| 5,954,049 A | 9/1999 | Foley et al. | |
| 5,988,160 A | 11/1999 | Foley et al. | |
| 6,024,120 A * | 2/2000 | Yam | A61M 1/0031 128/204.26 |
| 6,026,807 A | 2/2000 | Puderbaugh et al. | |
| 6,039,042 A | 3/2000 | Sladek | |
| 6,033,841 A | 4/2000 | Verdun et al. | |
| 6,044,841 A * | 4/2000 | Verdun | A61M 11/06 128/200.14 |
| 6,073,628 A | 6/2000 | Butler et al. | |
| 6,116,233 A | 9/2000 | Denyer et al. | |
| 6,116,239 A | 9/2000 | Volgyesi | |
| 6,129,080 A | 10/2000 | Pitcher et al. | |
| 6,131,568 A | 10/2000 | Denyer et al. | |
| 6,176,237 B1 | 1/2001 | Wunderlich et al. | |
| 6,179,164 B1 | 1/2001 | Fuchs | |
| 6,223,745 B1 | 5/2001 | Hammarlund et al. | |

(56) References Cited

U.S. PATENT DOCUMENTS

| | | | |
|---|---|---|---|
| 6,237,589 B1 | 5/2001 | Denyer et al. | |
| 6,253,767 B1 | 7/2001 | Mantz | |
| 6,293,279 B1 | 9/2001 | Schmidt et al. | |
| 6,338,443 B1 | 1/2002 | Piper | |
| 6,345,617 B1 | 2/2002 | Engelbreth et al. | |
| 6,435,177 B1 | 8/2002 | Schmidt et al. | |
| 6,450,163 B1 | 9/2002 | Blacker et al. | |
| 6,481,435 B2 | 11/2002 | Hochrainer et al. | |
| 6,513,519 B2 | 2/2003 | Gallem | |
| 6,543,448 B1 | 4/2003 | Smith et al. | |
| 6,557,549 B2 | 5/2003 | Schmidt et al. | |
| 6,578,571 B1 | 6/2003 | Watt | |
| 6,584,971 B1 | 7/2003 | Denyer et al. | |
| 6,595,203 B1 | 7/2003 | Bird | |
| 6,606,992 B1 | 8/2003 | Schuler et al. | |
| 6,612,303 B1 | 9/2003 | Grychowski et al. | |
| 6,644,304 B2 | 11/2003 | Grychowski et al. | |
| 6,679,250 B2 | 1/2004 | Walker et al. | |
| 6,698,421 B2 | 3/2004 | Attolini | |
| 6,708,688 B1 | 3/2004 | Rubin et al. | |
| 6,748,945 B2 | 6/2004 | Grychowski et al. | |
| 6,796,513 B2 | 9/2004 | Fraccaroli | |
| 6,823,862 B2 | 11/2004 | McNaughton | |
| 6,848,443 B2 | 2/2005 | Schmidt et al. | |
| 6,857,427 B2 | 2/2005 | Ziegler et al. | |
| 6,883,517 B2 | 4/2005 | Halamish | |
| 6,885,684 B2 | 4/2005 | Ichino | |
| 6,904,908 B2 | 6/2005 | Bruce et al. | |
| 6,929,003 B2 | 8/2005 | Blacker et al. | |
| 6,994,083 B2 | 2/2006 | Foley et al. | |
| 7,013,896 B2 | 3/2006 | Schmidt | |
| 7,036,505 B2 | 5/2006 | Bacon et al. | |
| 7,051,731 B1 | 5/2006 | Rogerson | |
| 7,080,643 B2 | 7/2006 | Grychowski et al. | |
| 7,131,439 B2 | 11/2006 | Blacker et al. | |
| 7,131,440 B2 | 11/2006 | Sonntag | |
| 7,201,165 B2 | 4/2007 | Bruce et al. | |
| 7,252,085 B2 | 8/2007 | Kunschir | |
| 7,255,106 B2 | 8/2007 | Gallem et al. | |
| 7,261,102 B2 | 8/2007 | Barney et al. | |
| 7,267,120 B2 | 9/2007 | Rustad et al. | |
| 7,270,123 B2 | 9/2007 | Grychowski et al. | |
| 7,404,400 B2 | 7/2008 | Lulla et al. | |
| RE40,591 E | 12/2008 | Denyer | |
| 7,458,372 B2 | 12/2008 | Feiner et al. | |
| 7,503,843 B1* | 3/2009 | Wilmoth | B60H 1/249 454/162 |
| 7,559,322 B2 | 7/2009 | Foley et al. | |
| 7,568,480 B2 | 8/2009 | Foley et al. | |
| 7,581,718 B1 | 9/2009 | Chang | |
| 7,634,995 B2 | 12/2009 | Grychowski et al. | |
| 7,748,385 B2 | 7/2010 | Lieberman et al. | |
| 7,758,886 B2 | 7/2010 | Jauernig et al. | |
| 7,954,487 B2 | 6/2011 | Grychowski et al. | |
| 8,113,194 B2 | 2/2012 | Boehm et al. | |
| 8,333,190 B2 | 12/2012 | Addington et al. | |
| 8,342,171 B2 | 1/2013 | Boehm et al. | |
| 8,347,878 B2 | 1/2013 | Schuschnig et al. | |
| 8,397,712 B2 | 3/2013 | Foley et al. | |
| D680,214 S | 4/2013 | Eckstein et al. | |
| 8,596,264 B2 | 12/2013 | Sommer | |
| 8,844,520 B2 | 9/2014 | Foley et al. | |
| 9,022,023 B2 | 5/2015 | Korneff | |
| 2002/0020762 A1 | 2/2002 | Selzer et al. | |
| 2002/0104531 A1 | 8/2002 | Malone | |
| 2002/0157663 A1 | 10/2002 | Blacker et al. | |
| 2003/0089366 A1 | 5/2003 | Sommer | |
| 2003/0136399 A1* | 7/2003 | Foley | A61M 11/06 128/200.14 |
| 2003/0159694 A1 | 8/2003 | McNaughton | |
| 2003/0197068 A1 | 10/2003 | Abate | |
| 2003/0209238 A1 | 11/2003 | Peters | |
| 2005/0039741 A1 | 2/2005 | Gallem et al. | |
| 2005/0145243 A1 | 7/2005 | Trombi | |
| 2005/0183718 A1 | 8/2005 | Wuttke et al. | |
| 2006/0011196 A2 | 1/2006 | Gallem et al. | |
| 2006/0157052 A1 | 7/2006 | Foley et al. | |
| 2007/0023036 A1 | 2/2007 | Grychowski et al. | |
| 2007/0068513 A1 | 3/2007 | Kreutzmann et al. | |
| 2007/0204864 A1 | 9/2007 | Grychowski et al. | |
| 2007/0235028 A1 | 10/2007 | Bruce et al. | |
| 2007/0289590 A1 | 12/2007 | Kreutzmann et al. | |
| 2008/0083407 A1 | 4/2008 | Grychowski et al. | |
| 2008/0230053 A1 | 9/2008 | Kraft | |
| 2008/0257345 A1 | 10/2008 | Snyder et al. | |
| 2009/0056716 A1* | 3/2009 | Carrier | A61M 15/00 128/204.15 |
| 2009/0272820 A1 | 11/2009 | Foley et al. | |
| 2011/0137290 A1 | 6/2011 | Flickinger | |
| 2011/0209700 A1 | 9/2011 | Kreutzmann et al. | |
| 2012/0266872 A1 | 10/2012 | Tanaka et al. | |
| 2012/0285447 A1 | 11/2012 | Schipper et al. | |
| 2013/0037020 A1 | 2/2013 | Tanaka et al. | |
| 2015/0231341 A1 | 8/2015 | Korneff | |

FOREIGN PATENT DOCUMENTS

| | | |
|---|---|---|
| DE | 8703534 U1 | 8/1987 |
| DE | 199 02 847 C1 | 5/2000 |
| DE | 199 53 317 C1 | 2/2001 |
| EP | 0 261 649 B2 | 9/1987 |
| EP | 0 281 650 A1 | 9/1988 |
| EP | 0 414 536 A2 | 2/1991 |
| EP | 0 281 650 B1 | 3/1992 |
| EP | 0 514 085 A1 | 11/1992 |
| EP | 0 587 380 | 3/1993 |
| EP | 0 601 708 A2 | 6/1994 |
| EP | 0 641 570 A1 | 3/1995 |
| EP | 0 711 609 A3 | 7/1995 |
| EP | 0 786 263 B1 | 1/1997 |
| EP | 0 855 224 B1 | 7/1998 |
| EP | 0 938 906 | 3/1999 |
| EP | 0 855 224 A2 | 7/1999 |
| EP | 0 601 708 B1 | 3/2000 |
| EP | 1 439 875 B1 | 10/2002 |
| EP | 1 673 124 B1 | 9/2004 |
| EP | 2 548 599 A1 | 2/2011 |
| FR | 1 070 292 | 7/1954 |
| FR | 93306974.2 | 3/1993 |
| FR | 2 763 507 A1 | 11/1998 |
| GB | 497 530 | 12/1939 |
| GB | 675524 | 7/1952 |
| GB | 2 253 200 A | 9/1992 |
| GB | 2 299 512 A | 10/1996 |
| GB | 2 310 607 A | 9/1997 |
| WO | 88/03419 A1 | 5/1988 |
| WO | 90/09203 | 8/1990 |
| WO | WO 92/15354 | 2/1992 |
| WO | 94/17753 A1 | 8/1994 |
| WO | 98/26828 A2 | 6/1998 |
| WO | 98/41265 A1 | 9/1998 |
| WO | 98/44974 | 10/1998 |
| WO | 99/40959 A1 | 8/1999 |
| WO | 99/53982 | 10/1999 |
| WO | 00/59565 | 10/2000 |
| WO | WO 2011/135915 A1 | 11/2011 |
| WO | WO 2011/158715 A1 | 12/2011 |
| WO | WO 2011/158716 A1 | 12/2011 |
| WO | WO 2013/013852 A1 | 1/2013 |
| WO | WO 2013/099397 A1 | 7/2013 |
| WO | WO 2013/099398 A1 | 7/2013 |
| WO | WO 2013/099399 A1 | 7/2013 |
| WO | WO 2014/068387 A1 | 5/2014 |

OTHER PUBLICATIONS

Product Information, Boerhinger Ingelheim, "Introducing TORPEX™ (aerosol albuteral sulfate): The Ultimate Tool for Equine Inhalation Treatment", from website http://www.torpex.com/product_information/, Mar. 21, 2002, pp. 1-3.

PARI LC Plus Instructions for Use (GB), PARI GmbH, dated Jul. 2001.

(56) References Cited

OTHER PUBLICATIONS

Photographs of nebulizer manufactured by PARI GmbH with detachable gas flow interrupter believed to have been publicly available prior to Feb. 13, 1996.

* cited by examiner

Cross Section A-A

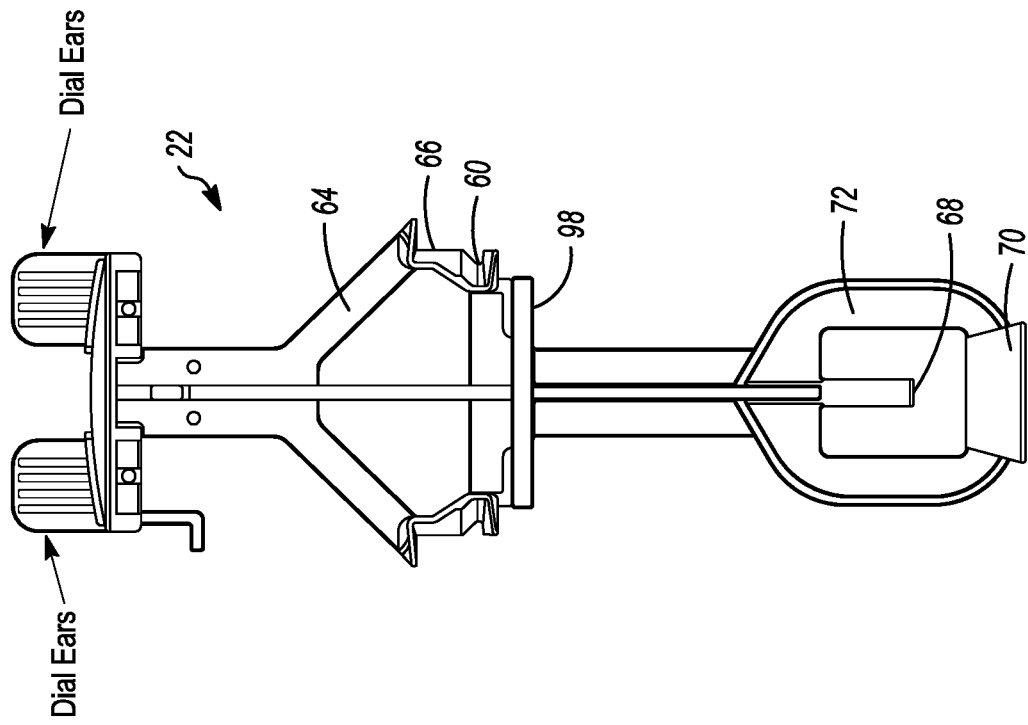
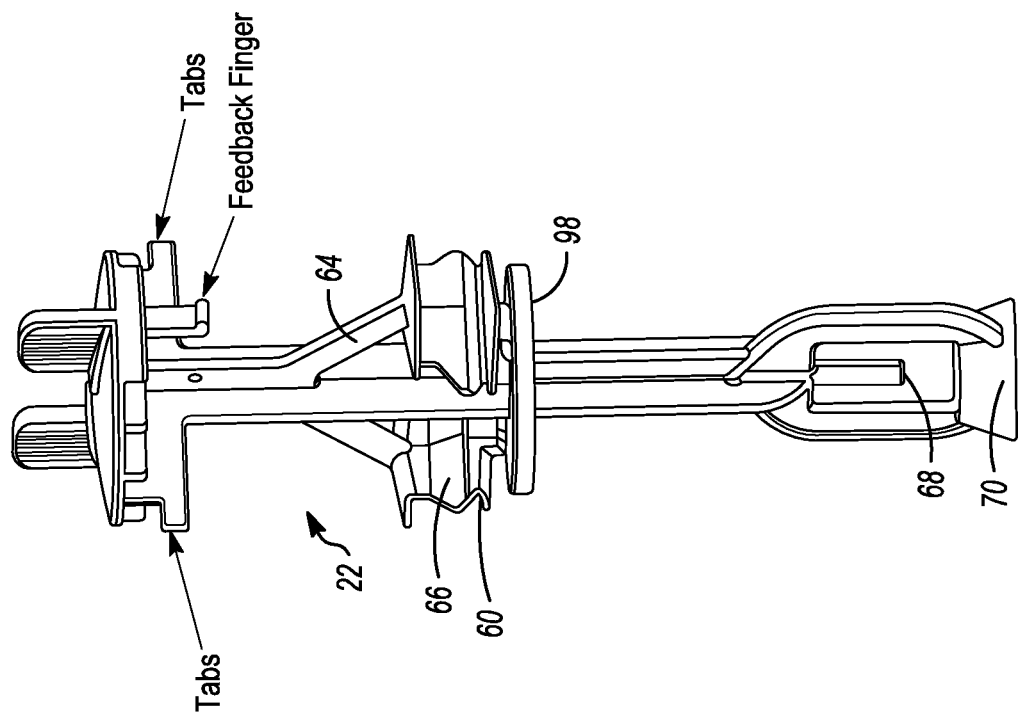

Breath Actuated Mode

Continuous Mode

Up Position

Up Position

NEBULIZER APPARATUS AND METHOD

CROSS-REFERENCE TO RELATED APPLICATIONS

This application claims the benefit of U.S. Provisional Application No. 62/360,165, filed Jul. 8, 2016, the entire disclosure of which is hereby incorporated herein by reference.

BACKGROUND

The present application relates to a method and apparatus for delivering an aerosol, nebulized liquid or solid medicine or a vapor to a patient's respiratory tract.

Medical nebulizers for generating a fine spray or nebula of a liquid medicine that can be inhaled by a patient are well known devices commonly used for the treatment of certain conditions and diseases. Nebulizers have applications in treatments for conscious, spontaneously-breathing patients and for controlled ventilated patients.

In some nebulizers, a gas and a liquid are mixed together and directed against a baffle. As a result, the liquid is aerosolized, that is, the liquid is caused to form into small particles that are suspended in the air. This aerosol of the liquid can then be inhaled into a patient's respiratory tract. One way to mix the gas and liquid together in a nebulizer is to pass a quickly moving gas over a liquid orifice tip of a tube. The negative pressure created by the flow of pressurized gas will draw the liquid out of the liquid orifice tip into the stream of gas and nebulize it.

Some of the considerations in the design and operation of nebulizers include regulation of dosages and maintenance of consistent aerosol particle size. In conventional nebulizer design, pressurized gas may entrain a liquid against a baffle on a continuous basis until the liquid in a reservoir is depleted. Continuous nebulization may result in a waste of aerosol during a patient's exhalation or during a delay between a patient's inhalation and exhalation. This effect may also complicate regulation of dosages because the amount of wasted aerosol may be difficult to quantify. Also, continuous nebulization may affect particle size and/or density. In addition, there may be excess medication lost to condensation on the nebulizer or mouthpiece during periods of non-inhalation. On the other hand, interrupted nebulization may also affect particle size and density as the nebulization is turned on and off.

BRIEF DESCRIPTION OF THE DRAWINGS

FIG. 26A is a perspective view of an actuator usable in the nebulizer of FIG. 1.

FIG. 26B is a side view of the actuator of FIG. 26A.

DETAILED DESCRIPTION

Figure 1:
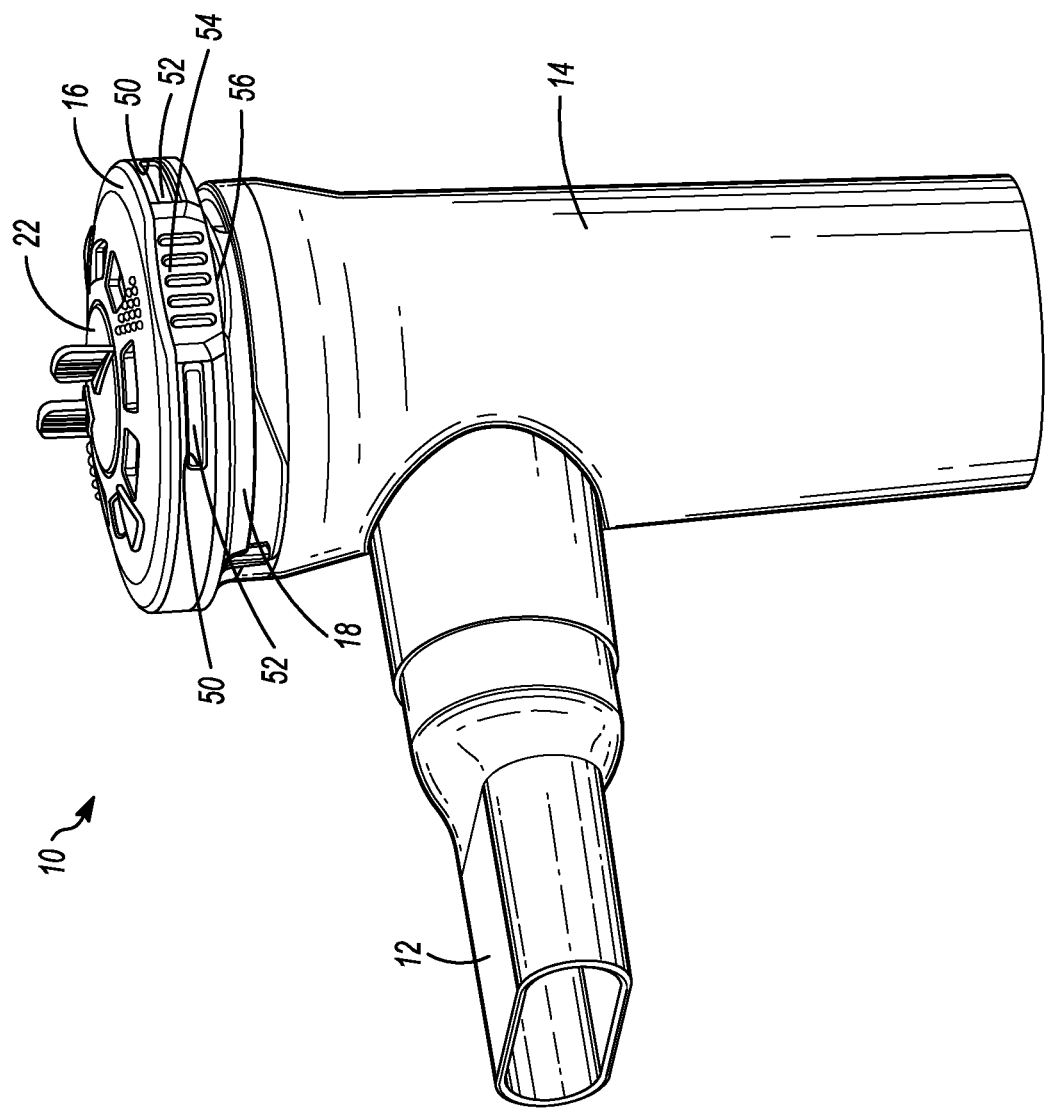
FIG. 1 is a side elevational view of a nebulizer according to the present invention.
Figure 2:
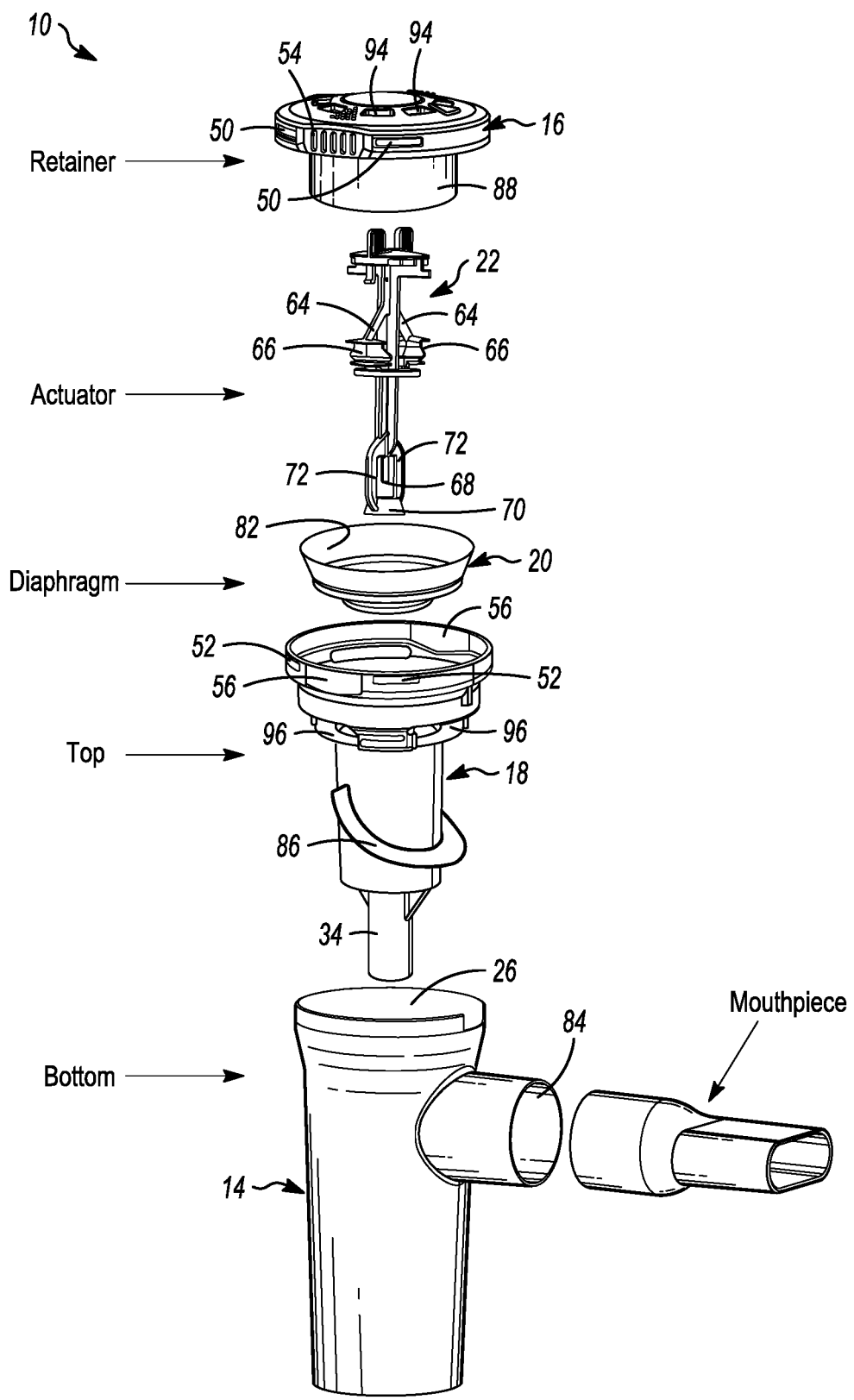
FIG. 2 is an exploded view of the nebulizer of FIG. 1.

A method and apparatus for delivering nebulized liquid or solid medication or vapor to a patient is disclosed.

The disclosed nebulizer design takes advantage a moving baffle concept, where the baffle is mounted to an actuator which has a constrained ability to move vertically within the nebulizer. Some known baffles may be incorporated into the top portion of the nebulizer and may require careful manual assembly in order to position the actuator within the nebulizer at a desired position in relation to the baffle. The travelling baffle design disclosed herein integrates the baffle into the actuator and may reduce the difficulties that may be experienced in manual assembly and may reduce the need for rotational orientation during assembly, thus allowing other components of the nebulizer to follow suit.

As described in greater detail below, a diaphragm includes a flexible membrane that responds to the changing pressures inside the nebulizer to drive the actuator and the baffle towards the pressured gas orifice, such that the baffle radially deflects gas injected into the nebulizer from a pressurized gas orifice outwards creating a low pressure zone over an adjacent liquid orifice. The capillary effect, along with the low pressure zone, draw the liquid from the reservoir in the nebulizer via the orifice and into the gas stream from the pressurized gas orifice. The diaphragm combines a biasing element, a latch feature to assemble the actuator with the diaphragm, an inhalation valve and an exhalation valve into a single part. The biasing element of the diaphragm is designed to provide assistance to the movement of the actuator. The amount of assistance needed from the diaphragm to move the actuator depends on a number of factors. These factors include the weight of the actuator, the upwards force created by the pressurized gas striking the baffle, any friction impeding the actuator, and any vacuum force generated by internal aerodynamics of the nebulizer.

The assistance the biasing element of the diaphragm provides to the movement of the actuator can be in one of two directions. The biasing elements can help to hold the actuator in the "normally off" condition with the biasing element being sufficiently strong enough to hold the actuator in an UP/OFF position even when pressured gas is not injected into the nebulizer through the pressured gas inlet. This biasing element is ideally responsive enough to quickly react to negative pressures generated though inhalation. Conversely, the biasing element could also be implemented to hold the actuator in the "normally on" condition when pressured gas is applied to the pressured gas inlet. The biasing element would be sufficiently weak to allow the actuator to move to the UP/OFF position when pressured gas is applied to the pressured gas inlet, yet strong enough to help the patient overcome the force imparted by the gas stream on the actuator and minimize the work needed to be done on inhalation.

In addition to the biasing member function of the diaphragm, the diaphragm includes two valves that may behave like pressure relief valves: an inner valve is a center opening valve positioned in to resist opening until the spring has collapsed and aerosol is being generated. Controlling the inhalation valve involves balancing between premature and delayed opening. Premature opening of the inhalation valve would increase the flow required to actuate, reducing the drug delivered per breath, and thereby increasing the overall drug delivery time. In an extreme situation, the nebulizer would fail to actuate and a delayed opening would make inhaling through the device more difficult since the user would need to impart more energy to sustain flow through the inhalation valve. In an extreme case, a user would not be able to generate enough vacuum to open the inhalation valve and no flow would be generated.

Also disclosed in the implementations provide herein are features such as an exhalation pathway that channels expired air out of the rear of the nebulizer, away from the patient, as well as a mode selector and methods of use. Various methods discussed herein allow for switching the nebulizer between a breath-actuated mode, where aerosol is only generated upon inhalation through the nebulizer mouthpiece, and a continuous mode, where the mode selector fixes the components of the nebulizer to continuously generate an aerosol as long as a pressurized gas is being supplied and a medicament is present in the reservoir.

Referring now to FIGS. 1-2, one implementation of a nebulizer 10 is shown. The nebulizer may include six discrete components (FIG. 2), five of which are capable of being assembled in a top-down method with each component (other than the mouthpiece 12) sharing a common central axis. This arrangement may assist with reducing complexity when implementing automated assembly. As can be seen, the components are also capable of being assembled manually and incorporate features to reduce a probability of human error in the assembly process.

The components of the nebulizer 10 include a bottom housing 14 having a cylindrical body. The nebulizer 10 also contains a top portion, referred to as the retainer 16, and an internal assembly, referred to as the inner housing 18. A flexible component is also included in the nebulizer 10, and is referred to as the diaphragm 20. A long, shaft-like component, referred to as the actuator 22, is also contained within the nebulizer 10. The final component is the tubular mouthpiece 12. The components of the nebulizer 10, other than the diaphragm 20, may be formed with a single piece of material by an injection molding process and assembled without the use of welding or adhesives and joined together using interference fits.

The retainer 16, actuator 22, inner housing 18, bottom hosing 14 and mouthpiece 12 may all be constructed from a plastic material such as, but not limited to, polypropylene. Any of a number of types of plastic may be used to construct these parts of the nebulizer 10. The diaphragm 20 may be constructed from, but not limited to, a flexible material such as silicone.

Referring to FIG. 6, a pressurized gas inlet 24 of the bottom housing 14 extends into the chamber 26 of the bottom housing 14. The external opening 28 of the pressured gas inlet 24 is designed to press-fit with a pressured gas hose fitting (not shown). Inside the bottom housing 14, the pressurized gas inlet 24 tapers down into a nozzle with a pressurized gas orifice 30 having a predetermined diameter. Preferably the gas inlet 24 is coaxial with the cylindrical body of the bottom housing 14 and extends through the bottom wall 32 of the chamber 26. The inner housing 18 incorporates a nozzle cover 34 that slides over the pressurized gas inlet 24 on the bottom housing assembly 14.

The nozzle cover 34 is a tapered tubular member with openings at either end. When positioned over the pressurized gas inlet 24, the space between the nozzle cover 34 and the pressurized gas inlet 24 creates at least one passageway 36 between the radial opening created by the gap between the nozzle cover 34 and the bottom wall 32 of the bottom housing 14 and the annular opening 38 defined by the outer diameter of the nozzle end of the pressurized gas inlet 24 and the inner diameter of the nozzle cover 34. To maintain the proper size of the annular opening 38 and position of the nozzle cover 34 over the pressurized gas inlet 24, triangular ribs 40 may be included on the inside surface of the nozzle cover 34 and are designed to cooperate with a ledge 42 of the pressurized gas inlet 24, formed near the tip to locate the nozzle cover 34 concentrically and maintain the passageway opening 44 between the lower edge of the nozzle cover 34 and the bottom wall 32 of the bottom housing 14.

Figure 4:
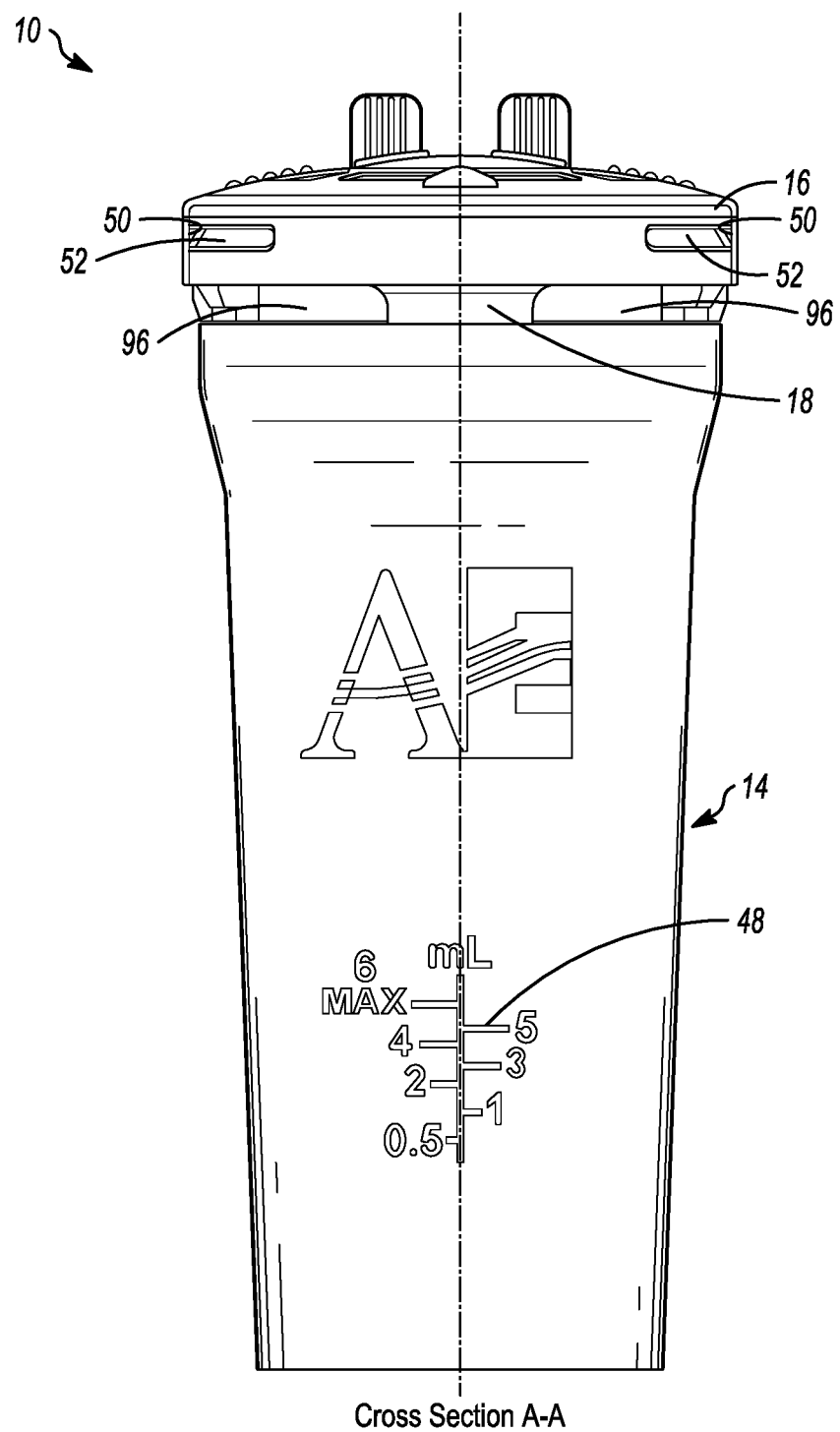
FIG. 4 is rear elevational view of the nebulizer of FIG. 1.
Figure 5:
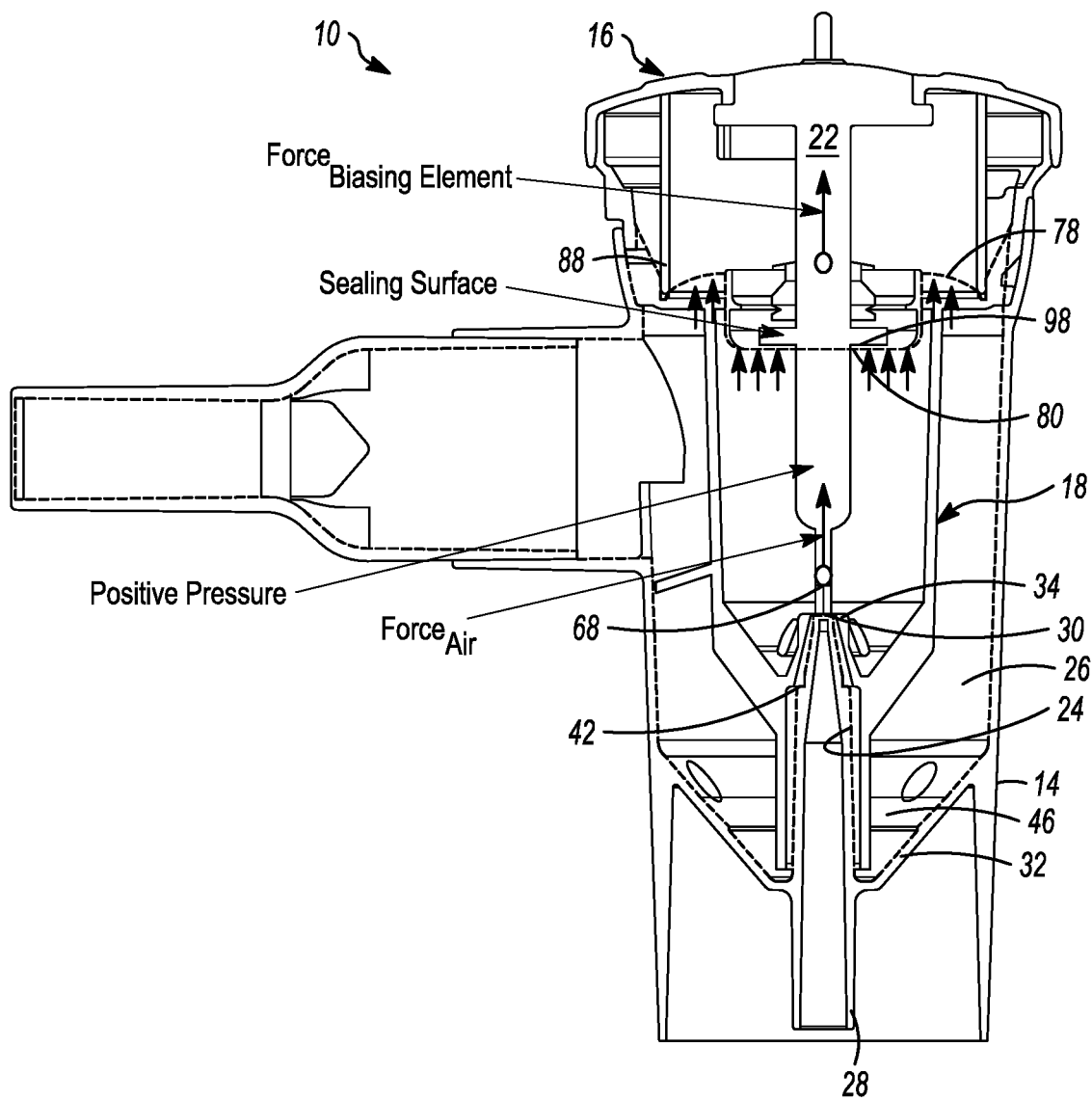
FIG. 5 is a cross-sectional view taken along line A-A of FIG. 4.
Figure 6:
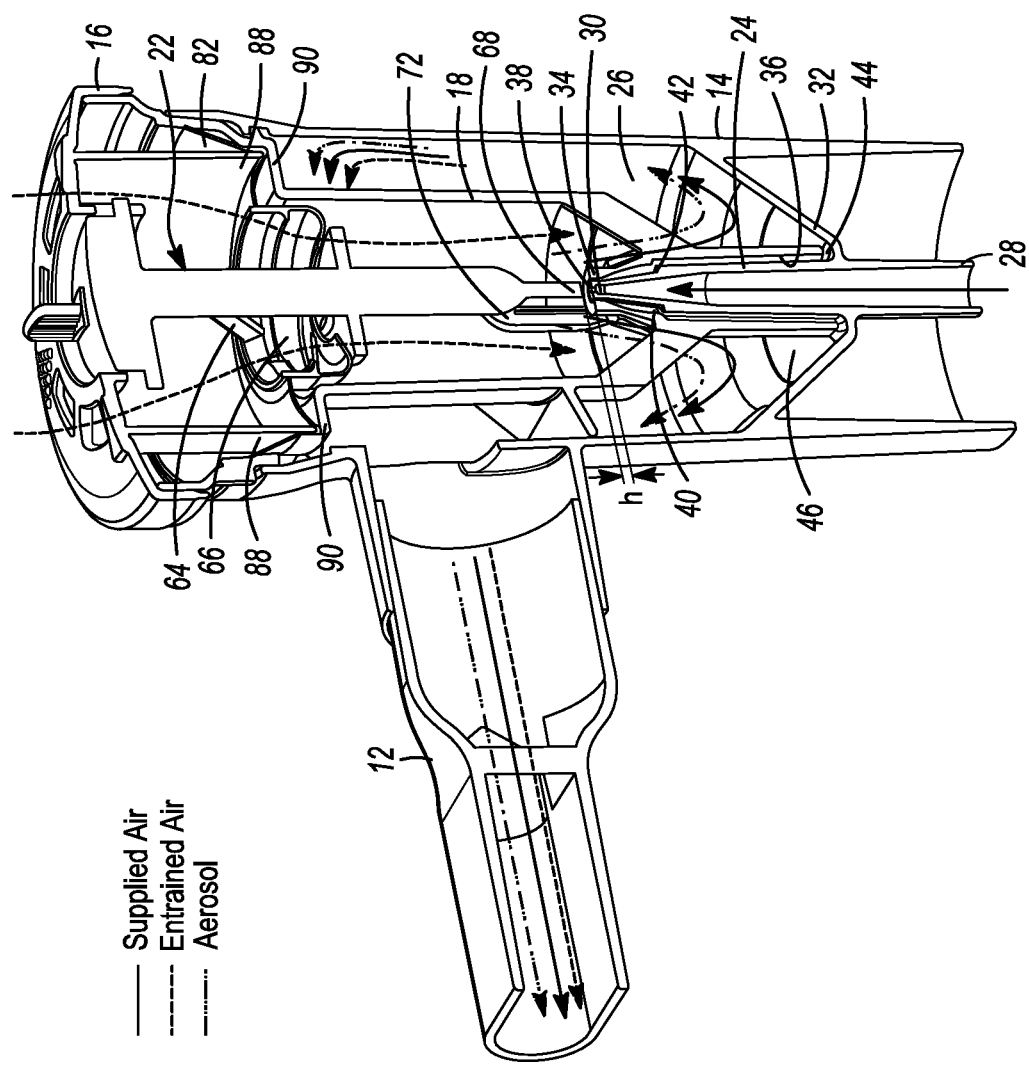
FIG. 6 is a perspective cross-sectional view of the nebulizer of FIG. 5.

The lower chamber of the bottom housing 14 is preferably used as a reservoir 46 and holds a fluid for nebulizing, such as a solution containing medication. In one embodiment, the lower wall of the bottom housing 14 slopes down to the base of the pressurized gas nozzle so that gravity urges the fluid into the reservoir 46, towards of the opening 44 of the passageway 36. As shown in FIGS. 5-6, the wall of the reservoir may be set at an approximate angle of 45 degrees from the central axis of the nebulizer, although other wall angles can be used to reduce the residual volume of medication at the end of a treatment. The bottom housing 14 may be constructed from transparent plastic material to allow for the patient and medical personnel to monitor medication levels in the nebulizer 10. Referring to FIG. 4, markings 48 are included on the outside surface of the bottom housing 14, in-line with the reservoir to show the user the fill volume of medication within the reservoir inside the bottom housing 14.

Referring to FIGS. 4, 6 and 8-10, the passageway 36 formed between the pressurized gas inlet 24 and nozzle cover 34 guides fluid from the reservoir 46 through the opening 44 to the passageway 36 and to the annular orifice 38. In this configuration, the flow of a fluid through the passageway 36 and the flow of a pressured gas through the pressurized gas inlet 24 are roughly parallel. The initial portion of the passageway 36 through which fluid (for example a liquid) travels is an annular or cylindrical pathway that may be undivided vertically. The ribs on the nozzle cover 34 of the internal housing 18 that maintain the concentricity and height of the nozzle cover 34 with respect to the pressurized gas inlet 24 may divide the passageway 36 into three (3) separate passages near the tip of the nozzle cover 34, however the separate passages merge and become undivided past the ribs, prior to the pressurized gas orifice 30. The characteristics of the aerosol generated in the nebulizer 10, in addition to the mass output of the nebulizer, may be varied by varying the size of and number of these passages near the end of the passageway 36, as well as by extending the passages to the surface of the pressurized gas orifice 30. Other passageway dimensions and arrangements may be implemented to achieve the desired aerosol size and density during nebulization. The pressured gas orifice 30 is preferably circular in shape and concentrically aligned inside the annular orifice 38 in communication with the passageway 36.

The tip of the nozzle cover 34 and tip of the pressurized gas inlet 24 may be flat surfaces. In one implementation, the pressurized gas orifice 30 is positioned in the plane of the annular orifice 38. Alternatively, the plane of the gas orifice 30 may be parallel to, and offset from, the plane of the tip of the nozzle cover. The relative heights (offsets) of the tips of the pressurized gas inlet 24 and the nozzle cover 34 may be varied to achieve the desired nebulization characteristics.

On the opposite end of the bottom housing 14 from the pressurized gas inlet 24, the inner housing 18 is removably attached to the cylindrical wall of the bottom housing 14 through the use of three (3) equidistantly separated ledges on both the bottom housing 14 and inner housing 18 to which the inner housing 18 may be loosely rotated under for a frictional fit to the bottom housing 14. Rotational orientation of the inner housing 18 relative to the bottom housing 14 may be controlled by a tab incorporated into the inner housing 18 and a corresponding flat surface on the bottom housing 14 which arrests the rotational motion of the inner housing 18 when positioned correctly. A ramp profile in the bottom housing 14 ensures the ledges on the inner housing 18 move under the ledges on the bottom housing 14 as the tab follows the ramp profile. Though this example utilizes three (3) equidistantly spaced ledges around the outer surface of the bottom housing 14 and inner housing 18, any number of these threaded features may be used to the same effect in other implementations. When assembled, the outer surface of the inner housing 18 forms an interference fit with the inner surface of the bottom housing 14 to ensure that air and aerosol is unable to leak between the two components and into the ambient environment.

The outer flange of the retainer 16 contains four (4) cut-outs 50 which snap fit with corresponding male extrusions 52 on the outer surface of the inner housing 18 to assemble the retainer 16 to the inner housing 18. Two (2) textured flats 54 are included on the outer surface of the retainer 16 that break the circular profile of the outer flange, which aid in the assembly of the inner housing 18 to the bottom housing 14 as they mate with corresponding flats 56 on the outer surface of the inner housing 18. This aids in the implementation of automated assembly as the flats 54, 56 provide features for robotic assembly systems to grasp as well as for determining orientation with vision systems and reduce the probability of human error on assembly. The flats 54, 56 on the inner housing 18 and retainer 16 also allow the parts to be bowl fed to an automated assembly. The retainer 16 is designed such that the retainer 16 may be assembled to the inner housing 18 in either of the configurations possible that allow the flats on the inner housing 18 and bottom housing 14 to be parallel to each other on assembly as the features of the retainer 16 are symmetrical. The flats 54, 56 also help to hold the rotational orientation of the retainer 16 relative to the inner housing 18 after assembly.

Referring to FIGS. 2 and 5-8, the diaphragm 20 and retainer 16 are assembled coaxially and are mounted to each other through an interference fit between the actuator 22 latch feature of the diaphragm 20 and the receiving geometry of the actuator 22. In this configuration, the actuator 22 may be assembled with the diaphragm 20 by inserting the actuator through the inner, circular opening of the diaphragm 20 for a grommet style connection. A triangular-shaped ridge 58 around the surface of the inner opening 60 of the diaphragm 20 mates with complementary receiving triangular grooves 62 on the latching surface of the diaphragm 20. The actuator 22 incorporates two (2) curved surfaces of approximately equal diameter on the inner surface of the diaphragm 20 in this version of the latch feature.

When pushed through, the ridges slide into the receiving grooves on the actuator 22 and weakly hold the diaphragm 20 in place, relative to the actuator 22. The amount of interference between the actuator 22 and diaphragm 20 is an important element of the design as excessive force can cause deformation of the diaphragm 20, affecting the flow characteristics of the valves. No rotational orientation is required for the assembly of the diaphragm 20 and the actuator 22. There exists only a top-down orientation when assembling the diaphragm 20 to the actuator 22. Though only two (2) surfaces of contact 66 positioned at the end of support arms 64 extending from the central axis of the actuator 22, separated by 180 degrees around the common axis of the diaphragm 20 and the actuator 22, are used to stabilize the diaphragm 20, any number of such features could be used of various mating geometries though they are preferably equidistantly positioned around the actuator 22 to ensure the diaphragm 20 does not deform.

The diaphragm 20 and actuator 22 assembly is coaxially and slideably positioned within the nebulizer, inside the cavity created by the inner housing 18, with the coaxial body of the actuator 22 piston extending into the inner housing 18 along the longitudinal axis of the nebulizer as well as through a coaxial opening in the retainer 16 body. The closed, lower feature of the actuator 22 that extends into the cavity of the inner housing 18 defines a diverter 68 for diverting the flow of pressured gas emerging from the pressurized gas orifice 30. In one implementation, the diverter 68 has a flat, circular surface having a predetermined area. The surface is also preferably aligned parallel to the tip of the pressurized gas inlet 24 and perpendicular to the direction of flow of the pressurized gas through the pressurized gas orifice 30. Concentric alignment of the diverter 68 in relation to the pressurized gas orifice 30 is aided by a downward sloping flange 70 connected to the main actuator body with two arm protrusions 72. The downward sloping flange 70 acts as a guide and slides along the outer surface of the tapered end of the nozzle cover 34. The downward sloping flange 70 may be a short, tapered tubular feature with an opening at either end to allow pressured gas to travel unimpeded through its center, in addition to the tapered end of the nozzle cover 34. The flange 70 also helps to set a predetermined distance 'h' between the diverter surface and the surface of the pressurized gas orifice as the bottom of the flange 70 will contact a corresponding shoulder on the nozzle cover 34. The mouthpiece 12 is a tubular part with an ovular opening on one end for the patient to breathe through, and a cylindrical opening on the other end, that may be a 22 [mm] ISO standard fitting that is press-fit into the corresponding cylindrical tube extending from the bottom housing 14, perpendicular to the axis of assembly for all other components.

Figure 3A:
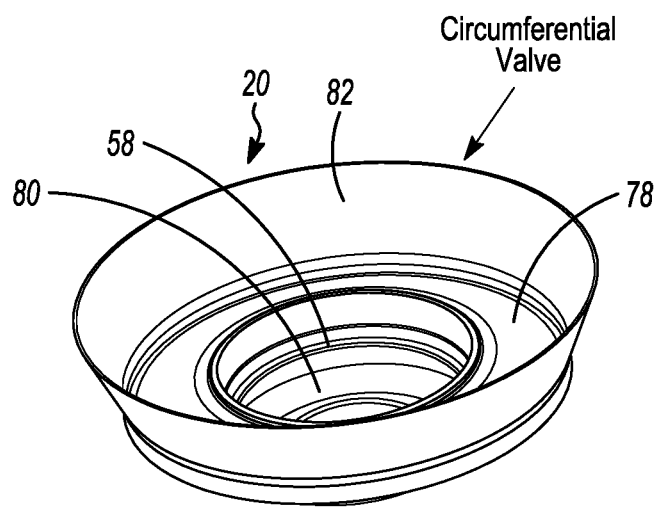
FIG. 3A illustrates an embodiment of a diaphragm including a combination of input valve, output valve and biasing member that is usable in the nebulizer of FIG. 1.
Figure 3B:
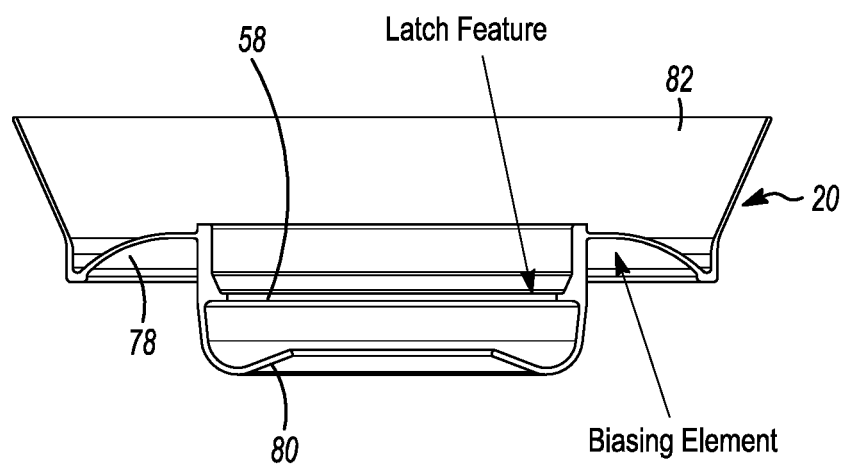
FIG. 3B is a cross-sectional view of the diaphragm of FIG. 3A.

Referring again to FIGS. 3A-3B, the diaphragm 20, a biasing element 78 is included along with inhalation and exhalation valves 80, 82 to control the flow of entrained air into the nebulizer 10 on exhalation and the flow of expired exhalation out of the nebulizer during exhalation by the patient. There are a variety of alternative embodiments of the diaphragm 20 contemplated in which these features may be incorporated that are further described below with respect to alternative configurations. The nebulizer 10 also includes a mechanism to allow for the nebulizer to be manually set to continually nebulize a fluid present in the reservoir 46 and to switch the nebulizer back to the breath actuated mode. Further details also are provided below. The nebulizer may also include an indicating feature to provide a visual verification on when nebulization is occurring.

Referring to the embodiment of FIGS. 1-11, the operation of the will now be explained. During operation, pressured gas provided from a gas source to the pressurized gas inlet 24 is continually entering the nebulizer 10 through the pressurized gas orifice 10. There are two main positions that the actuator 22 can be in that cover the two states of the nebulizer during operation. In the first position, the diverter 68 is spaced a great enough distance away from the top of the pressurized gas orifice 30 so that nebulization is not initiated. The second position occurs during inhalation (and in a continuous nebulization mode when that mode is manually set) and is achieved when the actuator 22 moves downward in relation to the rest of the nebulizer so that the diverter 68 moves to a predetermined distance 'h' from the orifice of the nozzle appropriate for nebulization of the fluid within the reservoir 46 to occur. The pressurized gas, which may be oxygen or any other breathable gas, continually flowing from the gas orifice 30 is now deflected radially outward from the gas orifice in a 360 degree pattern by the diverter 68. The gas fans out over the annular orifice 38 at a high velocity creating a low pressure zone over the annular orifice. The low pressure zone, along with the capillary effect, draws the liquid from the reservoir 46 though the passageway 36 and into the stream of the pressurized gas. The liquid is aerosolized and drawn out of the air outlet 84 in the bottom housing 14 through the mouthpiece 12.

To improve the performance of the nebulizer 10 in eliminating non-optimally size particles, the outer surface of the inner housing 18 may include an extension 86 that extends to the inner surface of the bottom housing 14 and at least part way around the outer circumference of the inner housing. The extension 86 acts to intercept oversized particles entrained in the gas flow and condense on the lower surface of the extension 86 and fall back into the reservoir 46. This also helps to decrease the number of oversized particles being inhaled through the mouthpiece. The extension also ensures ambient air that is drawn into the nebulizer takes a more circuitous route through the aerosol before it leaves the nebulizer. This may assist to limit the particle density and reduce the chance of particle growth through accidental particle collisions. As stated above, the actuator is required to move from the UP/OFF (non-nebulizing) position and the DOWN/ON (nebulizing) position for nebulization to occur. Inhalation of ambient air into the nebulizer via the mouthpiece 12 and the exhalation of expired air through the nebulizer and out to the ambient atmosphere and the resistance to this airflow are important factors which must be controlled to minimize the work required to be done by the patient during a treatment.

The biasing element 78 integrated into the diaphragm 20 assists in the movement of the actuator 22 and is configured to ensure nebulization occurs on inhalation when in breath actuated mode yet remains off when inhalation is not occurring to reduce risk of medication released to the ambient environment. Minimizing the inhalation flow required to move the actuator 22 is desirable because lowering the flow required to actuate means that nebulization of the medication may start earlier during inhalation and stop closer to the end of exhalation, thus generating more aerosol in each breath and maximizing drug output. In the diaphragm 20 of FIGS. 1-11, the exhalation valve 82 is incorporated into the upwards sloping, circumferential valve of the diaphragm and acts as a one-way pressure relief valve.

Inhalation airflow passes through the center-opening inhalation valve 80. In this configuration the inhalation valve 80 uses a donut valve design. As stated previously, the use of an inhalation valve 80 that seals onto the actuator 22 results in assembly that requires no rotational orientation between the actuator 22 and diaphragm 20 with only a vertical orientation needing to be considered. The diaphragm 20 is pinned in place between a ring-shaped extrusion 88 (also referred to herein as an exhalation skirt) located on the retainer 16 and a sealing surface 90 on the inner housing 18. This diaphragm retention technique helps to maintain a constant resting position for the diaphragm 20, locates the diaphragm 20 concentrically within the nebulizer 10, separates the movement of the biasing element 78 from the circumferential exhalation valve 82 and isolates the exhalation flow pathway and the inhalation flow pathway. On inhalation, the exhalation flange contacts a sealing surface incorporated into the inner housing 18 and the pathway is blocked. When sufficient negative pressure has been reached, the donut-shaped inhalation valve 80 is pulled away from the sealing surface 98 of the actuator 22 and air can flow around the sealing surface 98, through the pathway created by the donut-shaped inhalation valve 80, and into the main cavity of the nebulizer 10. Openings 94 located in the retainer 16 and openings 96 in the inner housing 18 allow air to move from the nebulizer's main chamber and into and out of the nebulizer 10.

Referring to FIGS. 5-8 inhalation and exhalation flow paths within the nebulizer 10 will now be described. Prior to inhalation by the patient, there exists an upwards force acting (See FIG. 5) on the actuator 22, caused by the pressured gas entering the main chamber through the pressurized gas orifice 30 and striking the diverter 68. This upwards force raises the actuator 22 to its uppermost position, maintaining the diverter's 68 position away from the pressurized gas orifice 30, and thus in a non-nebulizing position. Maintenance of the uppermost position of the actuator is also helped by the spring characteristics of the biasing element 78 on the diaphragm 20 which biases the actuator 22 up and away from the pressured gas orifice 30. The pressured gas entering the nebulizer also creates a positive pressure within the nebulizer 10, pressing the inhalation valves against the sealing surface of the actuator. Visualization of the positive pressure acting on the diaphragm and the force of the pressurized gas on the diverter is displayed in FIG. 5.

On inhalation, the biasing element 78 of the diaphragm 20 rolls inward in response to negative pressure from within the nebulizer 10, acting on the lower surface of the diaphragm. This lowers the position of the actuator 22, bringing the diverter 68 closer to the pressured gas orifice 30 until the actuator 22 reaches the nebulizing position so that the diverter 68 it diverts the flow of the pressured gas. The negative pressure inside the nebulizer also opens the inhalation valve on the diaphragm, allowing atmospheric air to be drawn into the device to improve the delivery of fine particle mass and to maintain a low inhalation resistance to minimize the work needed to be done by the patient during inhalation. Atmospheric air is drawn into the nebulizer through openings 94 integrated into the retainer.

Figure 7:
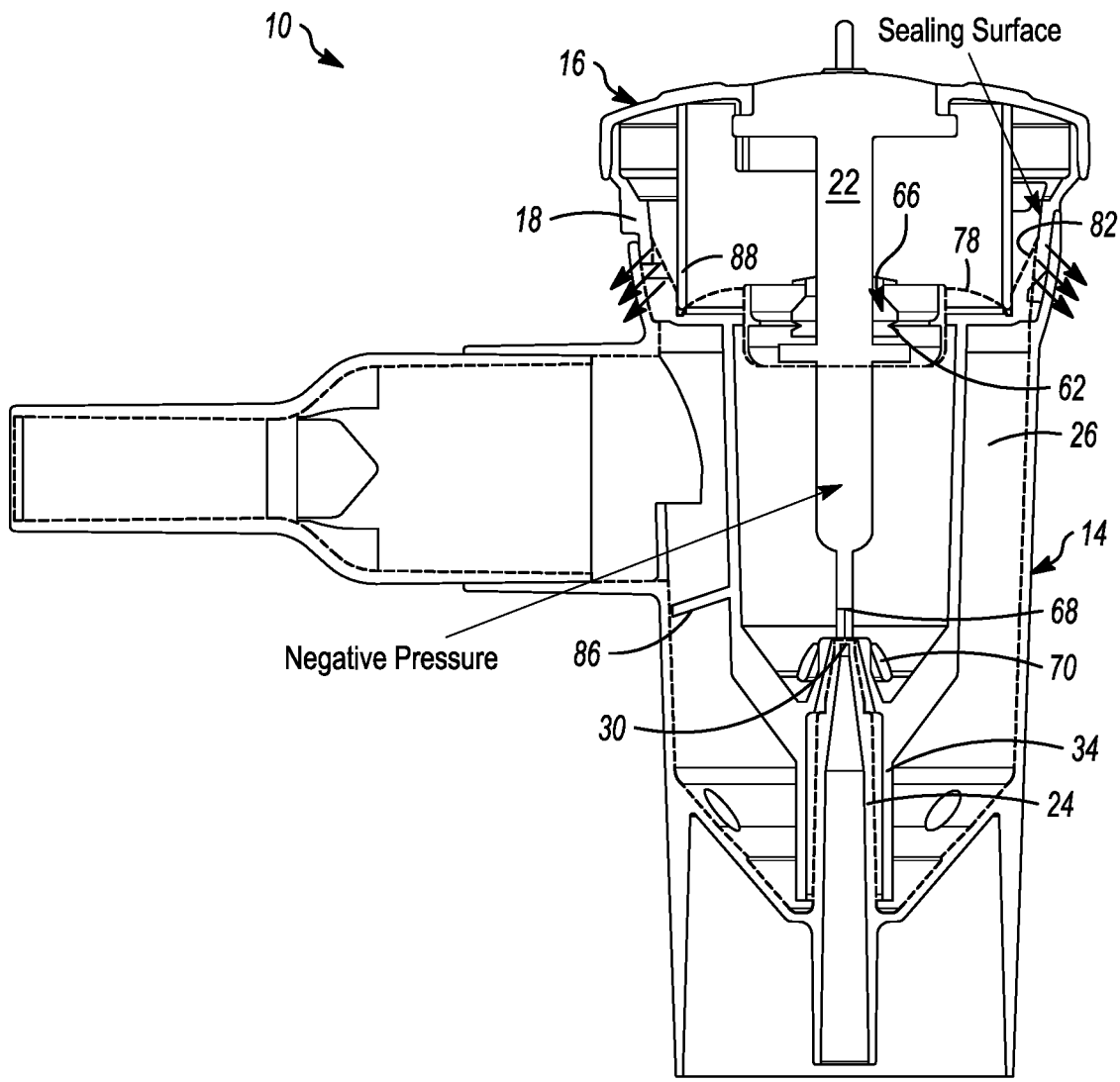
FIG. 7 is a cross-sectional view taken along line A-A of FIG. 4 illustrating a negative pressure zone in the nebulizer.
Figure 8:
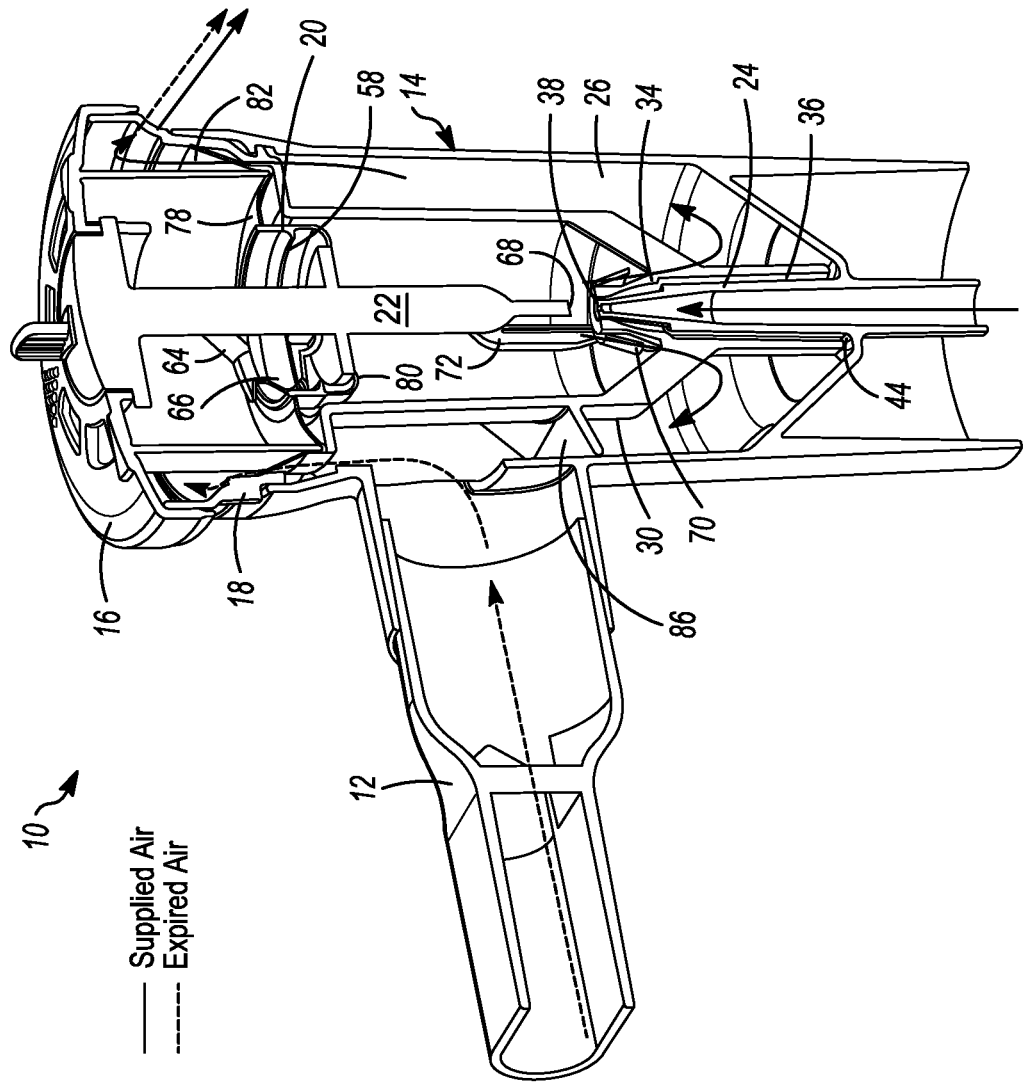
FIG. 8 illustrates the cross-sectional view of FIG. 6 with exhaled and supplied air pathways.
Figure 9:
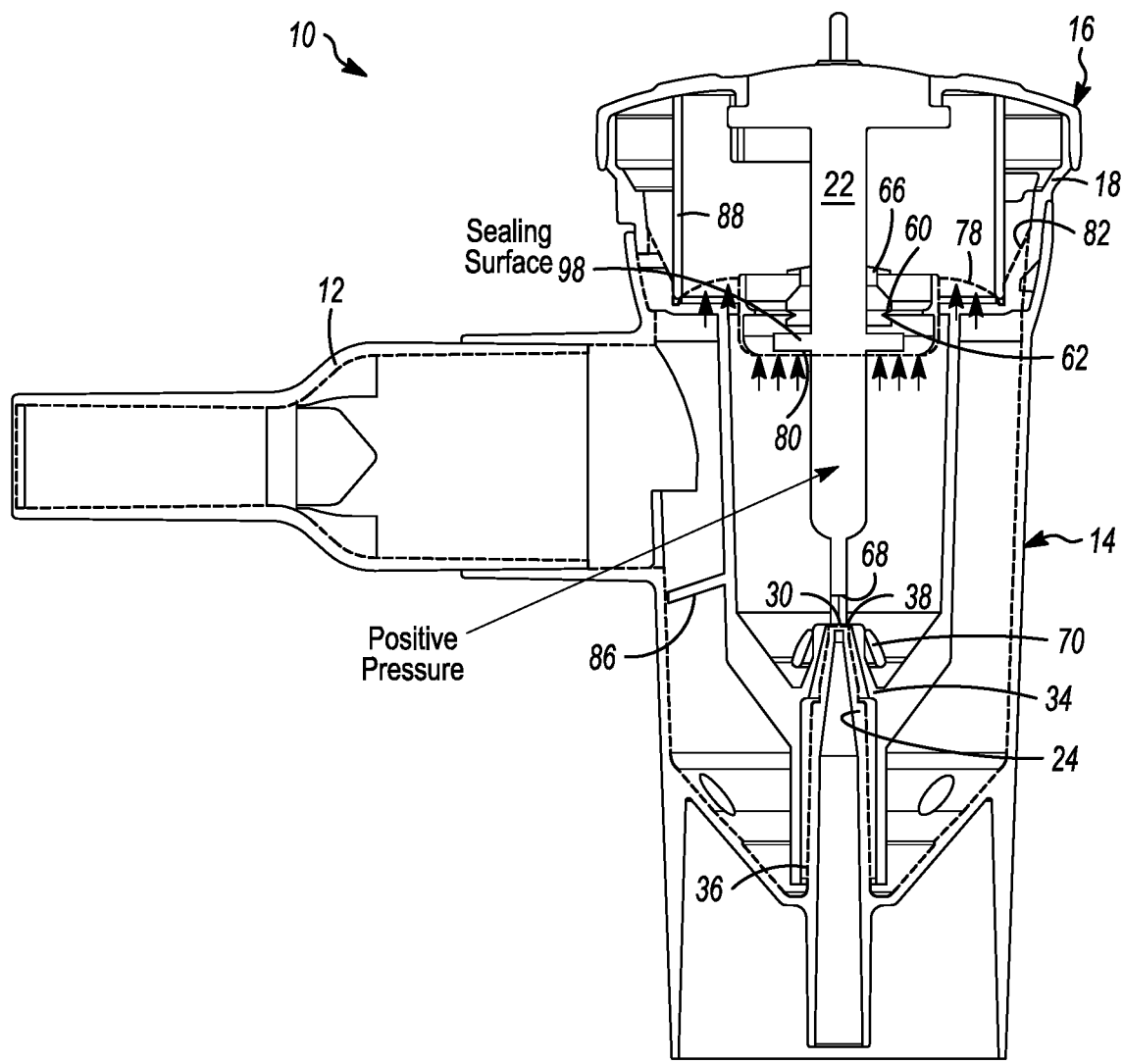
FIG. 9 illustrates the cross-sectional view of FIG. 7 with a positive pressure zone in the nebulizer.
Figure 10:
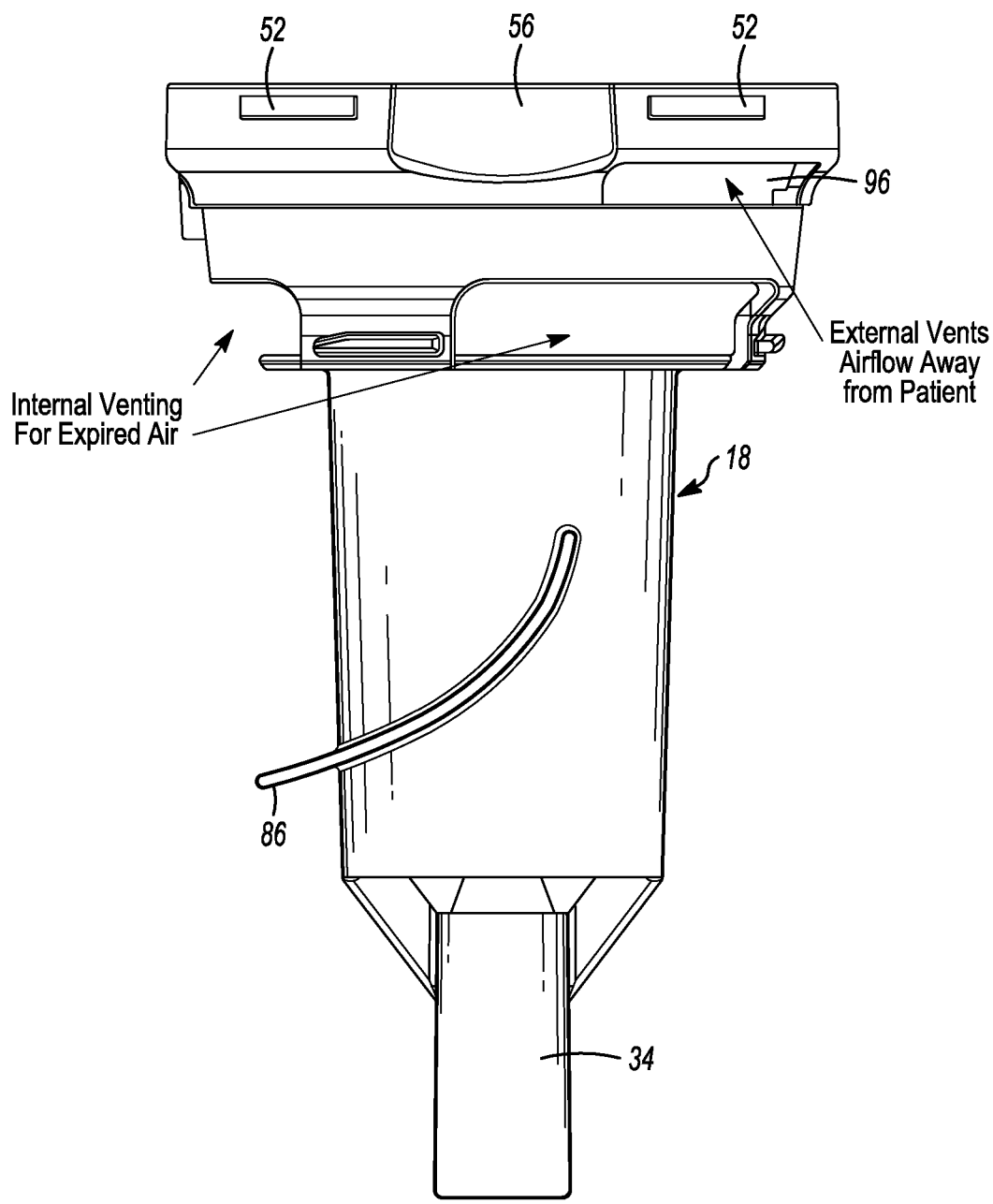
FIG. 10 is a side elevational view of an inner housing suitable for use in the nebulizer of FIG. 1.
Figure 11:
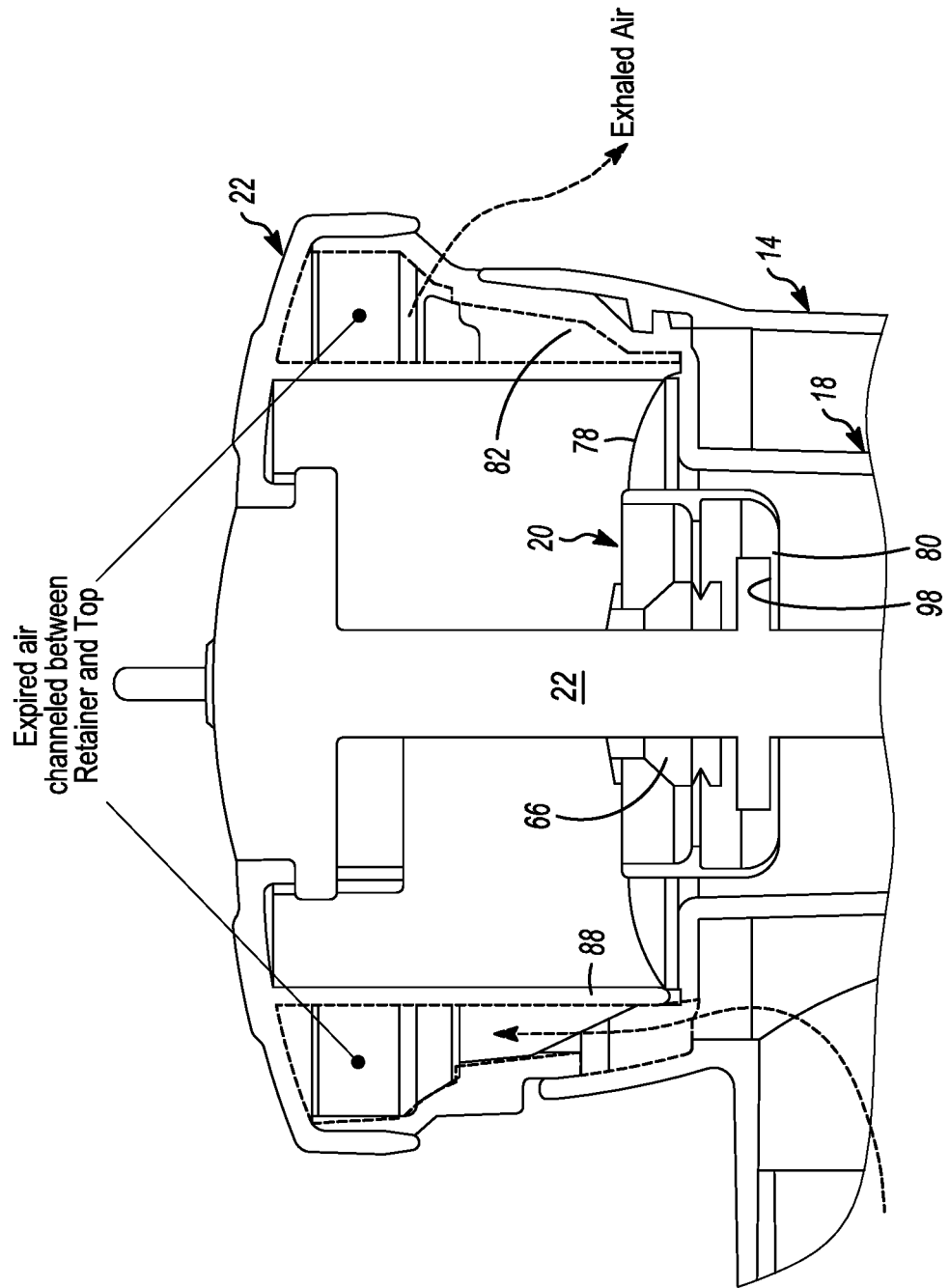
FIG. 11 is a partial cross-sectional view of the nebulizer of FIG. 17 illustrating an exhaled air pathway.

FIG. 6 illustrates the airflow pathways of the entrained air, supplied air and aerosol on inhalation. The negative pressure generated inside the device during inhalation also ensures that the outer circumferential exhalation valve 82 on the diaphragm 20 is sealed against the inner surface of the inner housing 18, blocking the exhalation pathway from inhalation airflow as shown in FIG. 7. FIG. 8 illustrates the airflow pathways of the expired air and supplied air on exhalation and FIG. 9 displays the effect of the positive pressure generated during exhalation on the inhalation valve 80. FIG. 10 shows the venting used to channel expired air out of the nebulizer 10 and away from the patient's face. FIG. 11 further highlights the isolation between inhalation and exhalation flow paths and the role of the exhalation skirt 88 in channeling the expired air out of the rear of the nebulizer and down away from the patient's face.

On exhalation, expired air moves through the nebulizer 10 and exits through the rear of the nebulizer, away from the patient, to ensure no medication is deposited on the patient's face or eyes. In one embodiment, two (2) rectangular windows 96 on the back and top of the inner housing 18 (See FIGS. 4 and 10) are used to allow the expired air to exit the nebulizer 10, however other variations in vent shape and sizing are contemplated. The vents 96 in the inner housing 18 allow both the supplied air and expired air to exit the main chamber 26 of the nebulizer 10 and move under the circumferential exhalation valve 82. Expired air is blocked from exiting the top windows 94 of the retainer 16 due to the exhalation skirt 88 pinning the diaphragm 20 to the inner housing 18, isolating the exhalation 82 and inhalation 80 valves. Airflow is channeled around the retainer 16 between the exhalation skirt 88 and inner housing 18 and vented out of the back of the nebulizer 10 through vents 96 incorporated into the inner housing 18. The positive pressure generated within the nebulizer seals the inhalation valve 80 against the sealing surface 98 of the actuator 22 and prevents air from flowing out of the top windows 94 of the retainer 18.

Second Embodiment

Figure 12A:
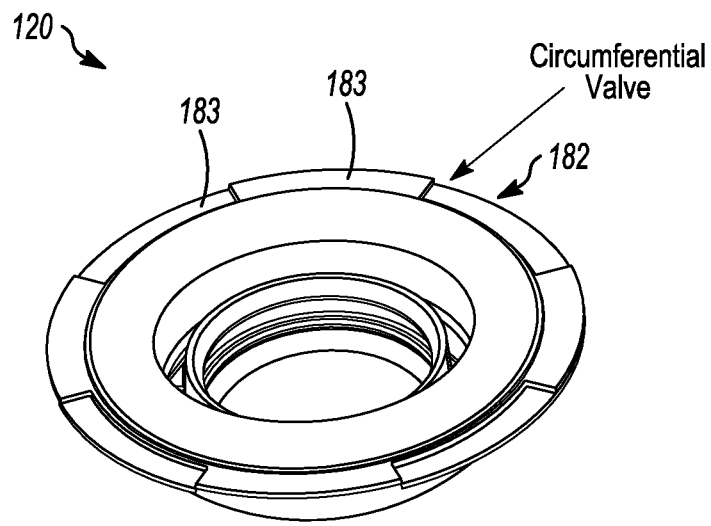
FIG. 12A illustrates an alternative embodiment of the diaphragm of FIG. 3A.
Figure 12B:
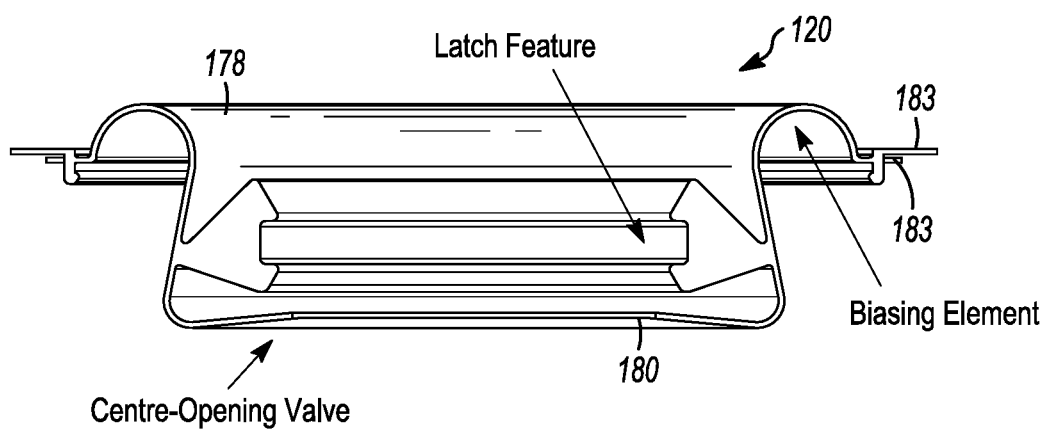
FIG. 12B is a cross-sectional view of the diaphragm of FIG. 12A

An alternative embodiment of the nebulizer 10 of FIGS. 1-11 is illustrated in FIGS. 12A-12B and 13A-13B. In this embodiment, air exhaled into the nebulizer 100 is directed through flaps on a circumferential exhalation valve ring 182 that forms part of the diaphragm 120. The exhalation valve ring 182 includes multiple flaps 183 that act as one-way pressure relief valves. Inhalation airflow passes through the center-opening inhalation valve 180 that reuses the previous embodiment's donut valve design. FIGS. 12A-12B illustrates one implementation of the relative positioning of all elements of the diaphragm 120. On inhalation, the exhalation flaps 183 contact a sealing surface 119 incorporated into the inner housing 118 and the exhalation pathway is blocked. When a sufficient negative pressure has been reached due to inhalation via mouthpiece 112, the inhalation valve 180 is pulled away from the sealing surface 198 of the actuator 122 and air can flow around the sealing surface 198, through the pathway created by the deformation of the inhalation valve 180, and into the main chamber 126 of the nebulizer 110. Windows/vents 194 located in the retainer 116 and inner housing 118 allow air to move to a from the nebulizer's main chamber 126 and into and out of the device. The biasing element 178, or the spring, of the diaphragm 120 is located between the actuator latch and the circumferential exhalation valve and is designed to have a resistance to motion that is sufficiently strong enough to hold the actuator 122 in the UP/OFF position until inhalation begins, yet responsive enough to quickly react to negative pressures generated through inhalation.

Figure 13A:
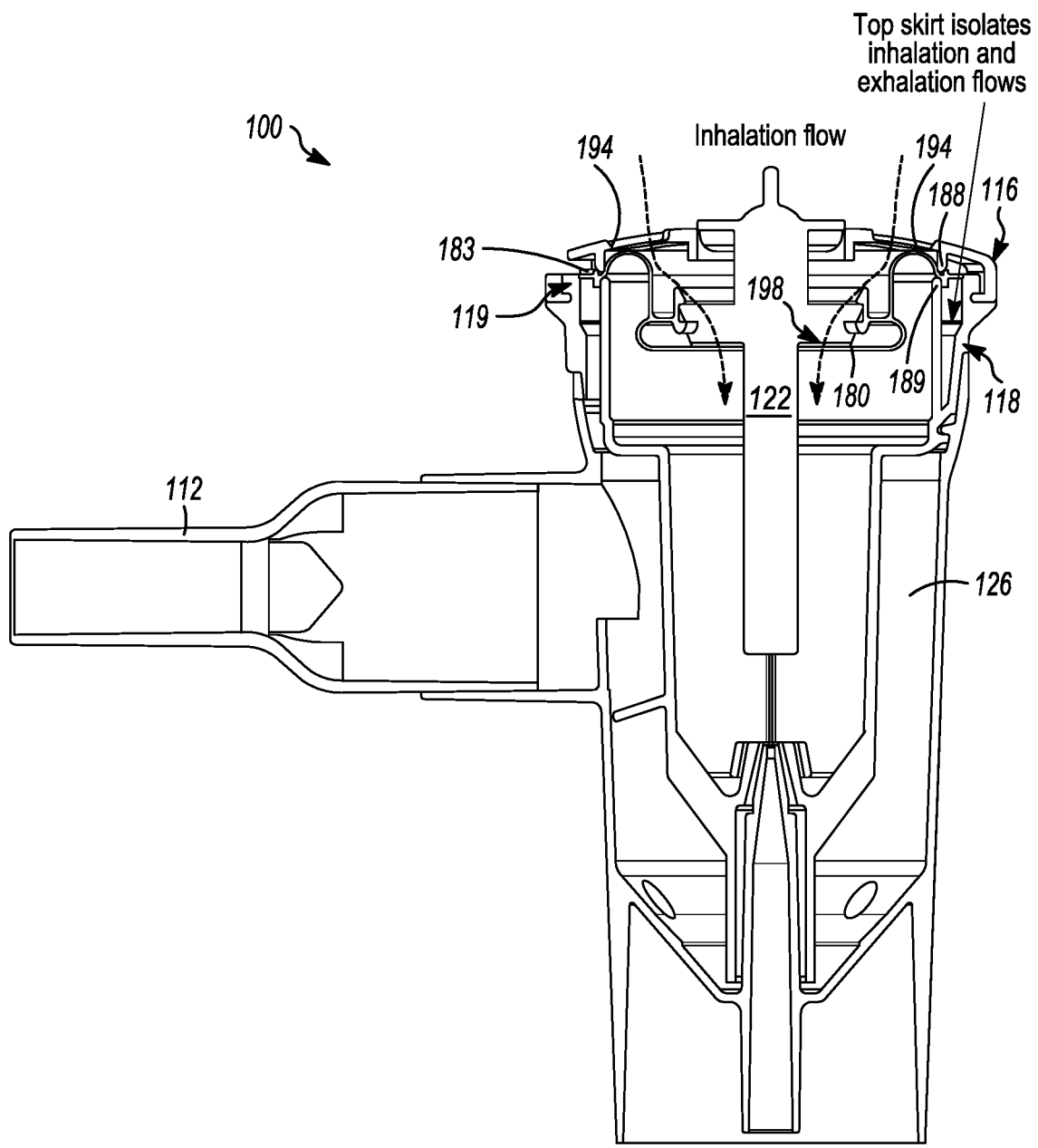
FIG. 13A is a cross-sectional view of a nebulizer utilizing the diaphragm of FIG. 12A showing an inhalation flow.
Figure 13B:
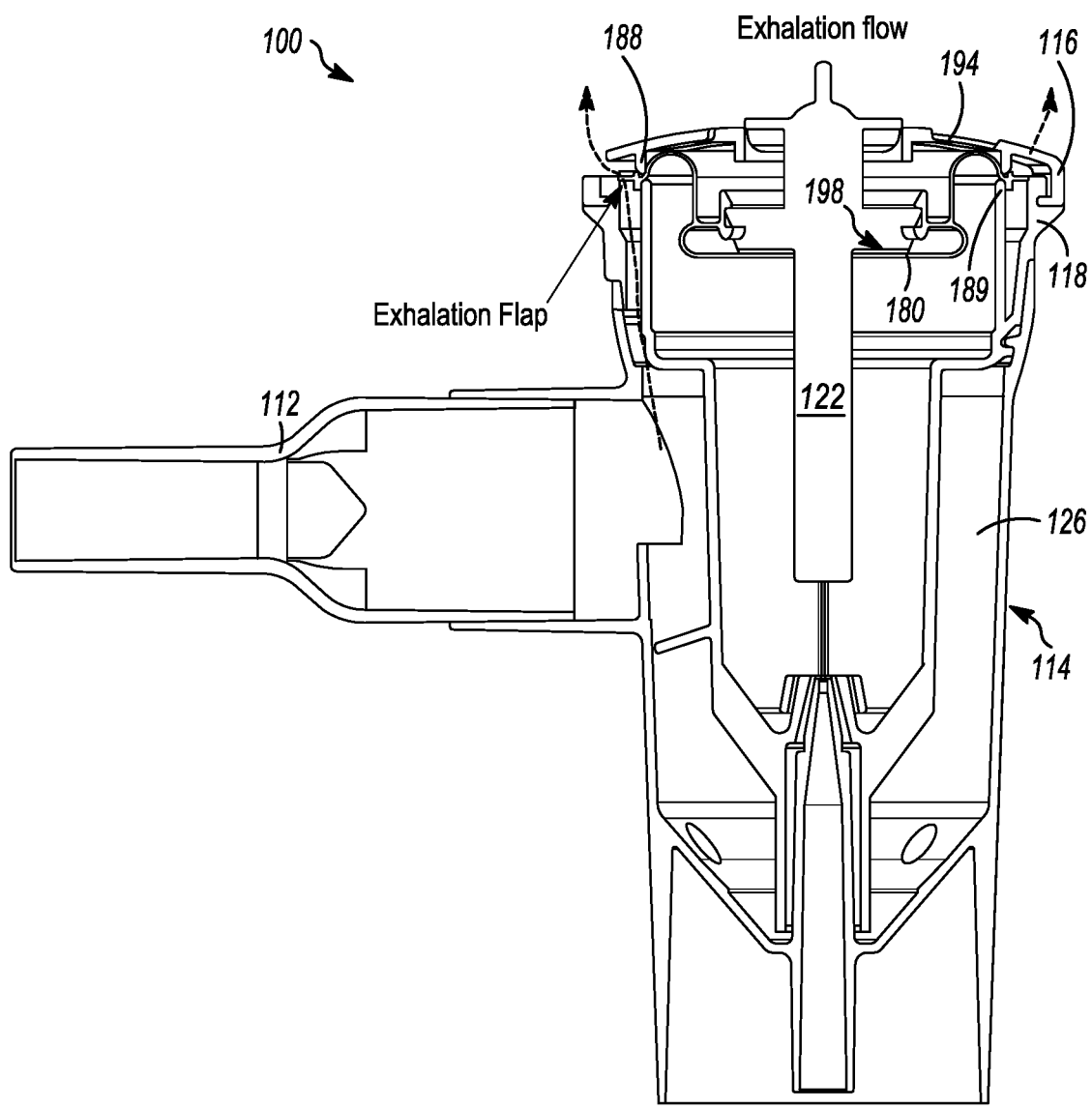
FIG. 13B is a cross-sectional view of a nebulizer utilizing the diaphragm of FIG. 13A showing an exhalation flow.

Referring to FIGS. 13A-13B, the biasing element 178 may be comprised of a flexible material having a concave-down geometry that rolls inward in response to negative pressure within the nebulizer, acting on the lower surface of the diaphragm 120. The diaphragm 120 is pinned in place between a ring shaped extrusion 189 located on the top of the inner housing 118 and a ring-shaped extrusion 188 formed on the retainer 116. This assembled configuration isolates the function of the exhalation valve 182 from that of the inhalation valve 180 and biasing element 178.

Referring again to FIGS. 12A-12B, the staggered flap 183 design of the exhalation ring 182 creates a notched valve with low exhalation resistance that may be manufactured using injection molding techniques. If the flaps 183 were instead all of equal height, and not offset or staggered as illustrated, notching of the exhalation ring valve would have created gaps between each flap, resulting in air leakage through the flap on inhalation. By dividing the circumference of the exhalation ring valve 182 into distinct flaps 183 of two (2) heights, a notched exhalation valve is created that can be molded with no undercut and no breaks in the seal on inhalation. In the example diaphragm 120 of FIGS. 12A-12B, the circumferential exhalation valve 182 is comprised of eight (8) equally sized flaps 183 however, an exhalation valve ring divided into any number of flaps with any number of distinct staggered heights is contemplated.

Third Embodiment

Figure 14A:
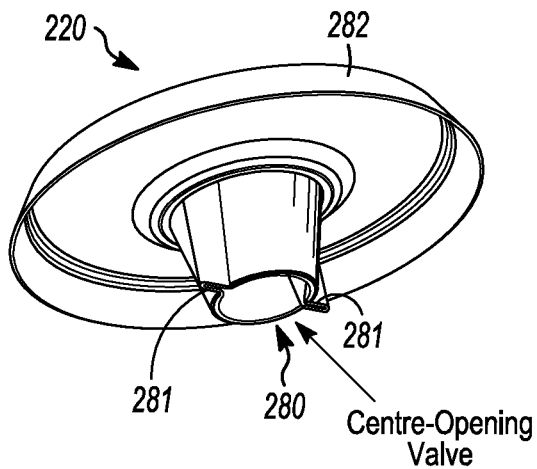
FIG. 14A is a bottom perspective view of a second alternative embodiment of the diaphragm of FIG. 3A.
Figure 14B:
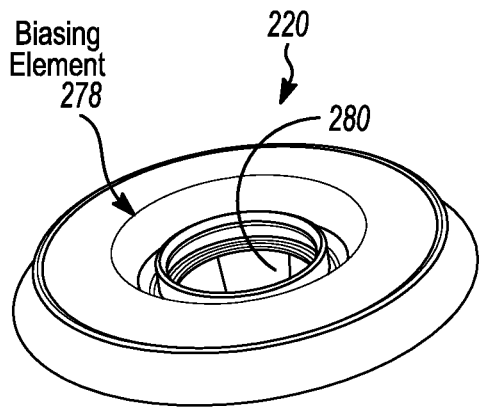
FIG. 14B is a top perspective view of the diaphragm of FIG. 14A.
Figure 14C:
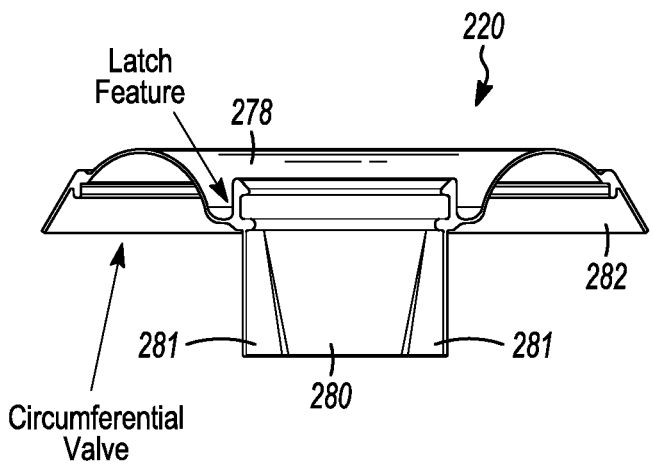
FIG. 14C is a cross-sectional view of the diaphragm of FIGS. 14A-14B.

In another embodiment, as shown in FIGS. 14A-C and 15-16, the diaphragm 220 may include an exhalation valve 280 that is a downward sloping, circumferential valve and acts as a one-way pressure relief valve. In contrast to the donut-type valve configuration discussed in the prior embodiments, inhalation airflow for the embodiment of FIGS. 14A-14C is controlled through a center-opening valve comprised of a modified duckbill check valve 280. Unlike traditional duckbill check valves that are self-sealing, this valve seals on the surface of the actuator 222. The circumference of the sealing surface 298 between the actuator 222 and duckbill valve 280 may be tailored to control inhalation resistance. The extra material allowance of the valves, shown in FIGS. 14A and 14C as the flat sections 281 of the valve 280, may be selected to control the opening of the valve 280 itself and affect factors such as inhalation resistance.

As with the other center-opening valves discussed previously, this design requires no rotational orientation between the actuator 222 and diaphragm 220 on assembly and only has vertical orientation requirements, such as to align with the sealing surface 298 on the actuator 222. The diaphragm 220 may be pinned in place between ring shaped extrusions 289, 288 located on the inner housing 218 and retainer 216, respectively. The configuration of the nebulizer 210 having the diaphragm 220 pinned as illustrated in FIGS. 15-16 helps isolate the movement of the exhalation valve 282 from the inhalation valve 280 and biasing element 278.

Figure 15:
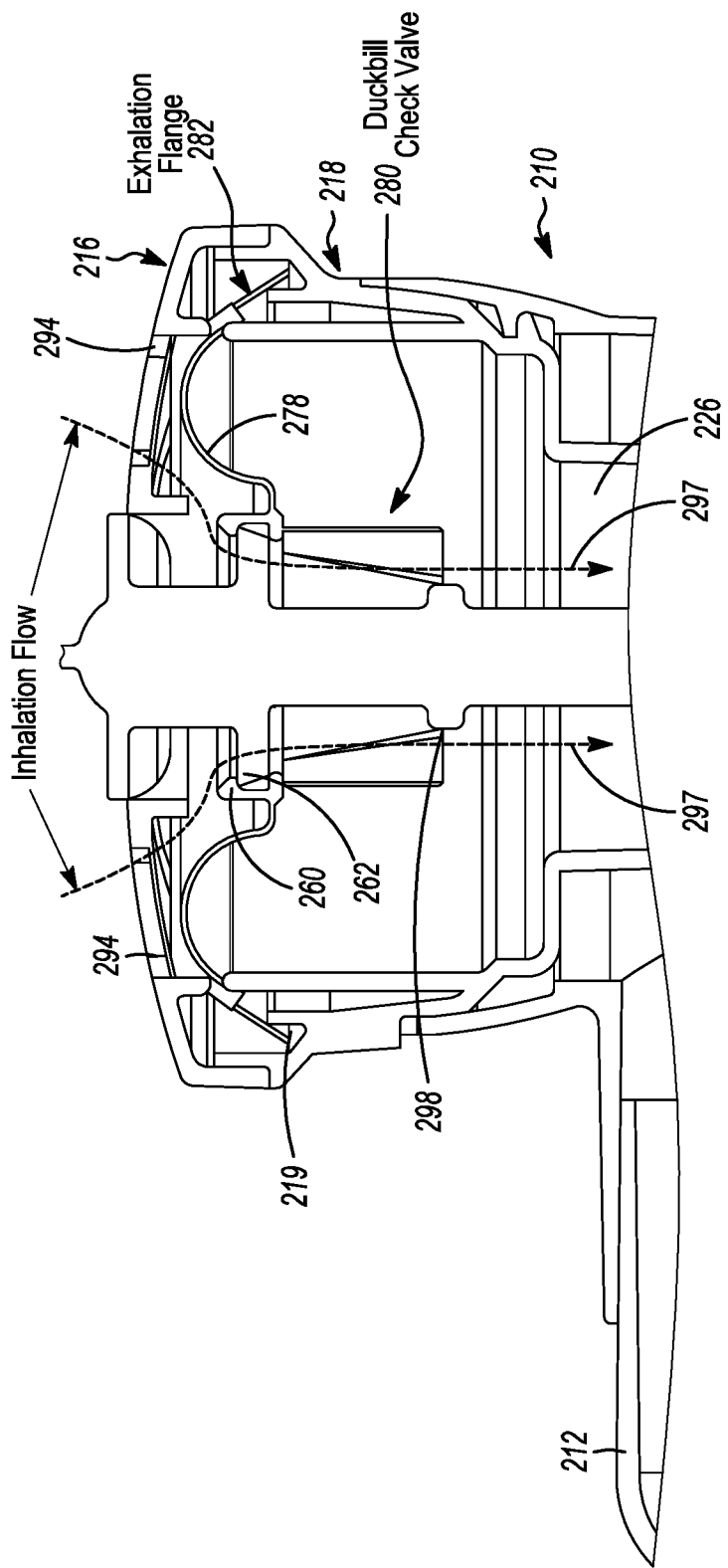
FIG. 15 is a partial cross-sectional view of a nebulizer utilizing the diaphragm of FIGS. 14A-14C illustrating an inhalation flow.
Figure 16:
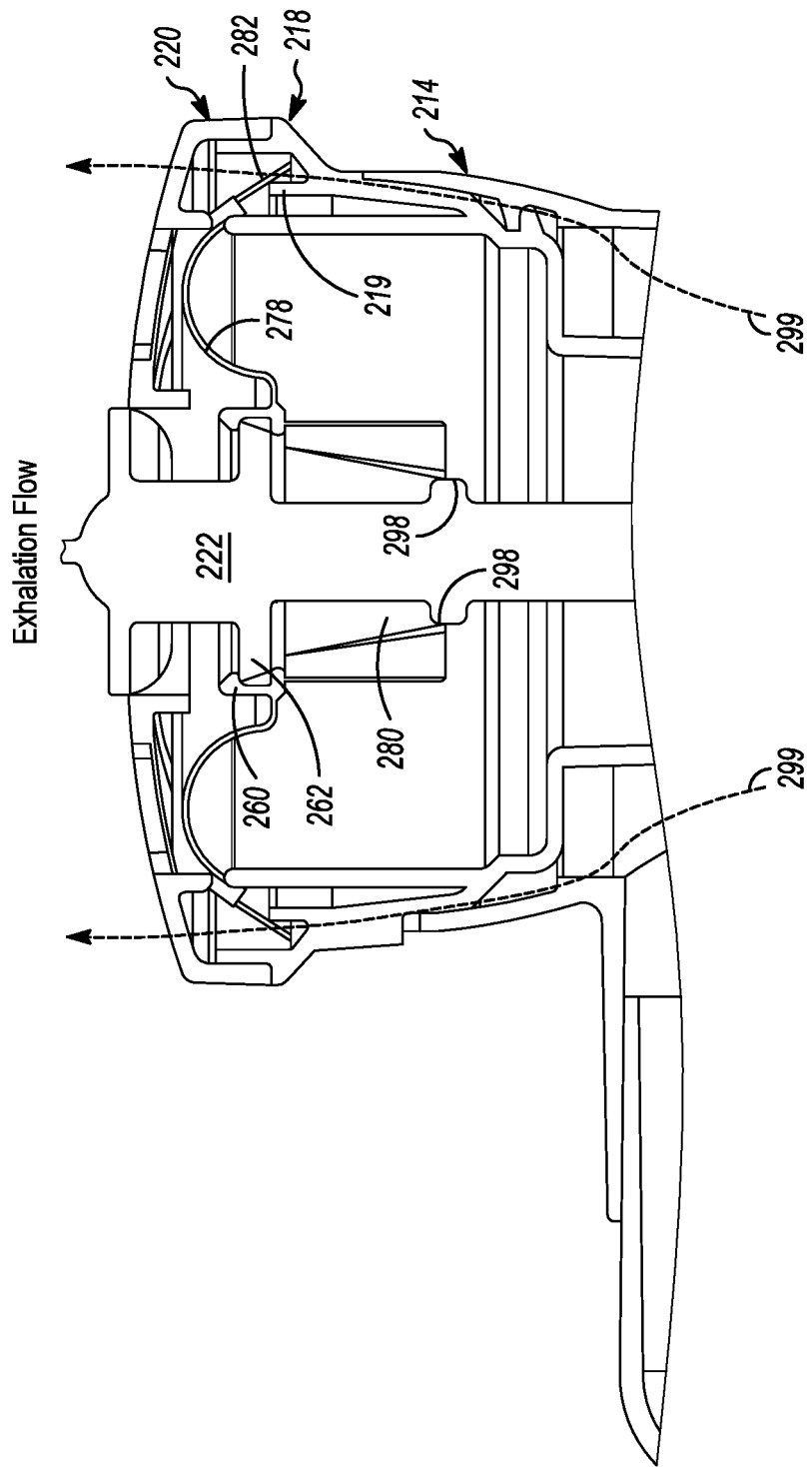
FIG. 16 is the partial cross-sectional view of the nebulizer of FIG. 15 illustrating an exhalation flow.
Figure 17A:
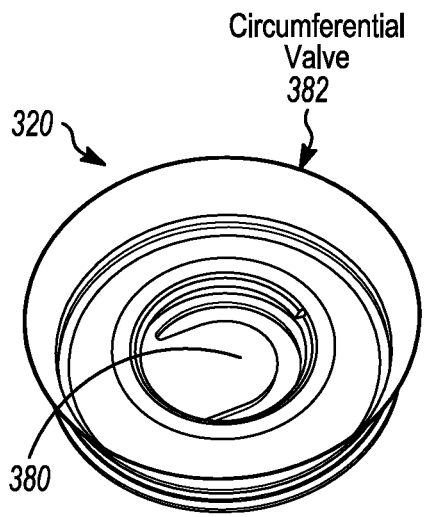
FIG. 17A is a top perspective view of a third alternative embodiment of the diaphragm of FIG. 3A.
Figure 17B:
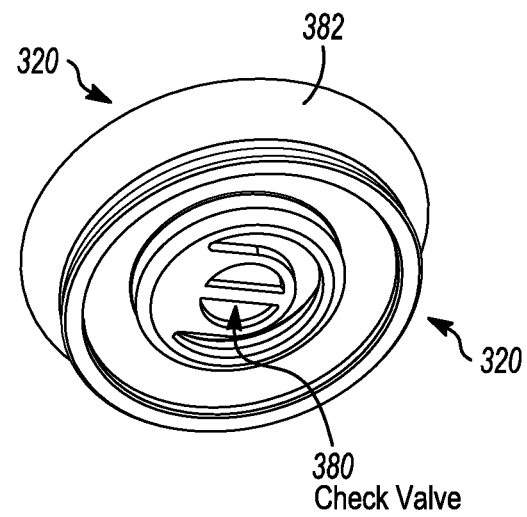
FIG. 17B is a bottom perspective view of the diaphragm of FIG. 17A.
Figure 17C:
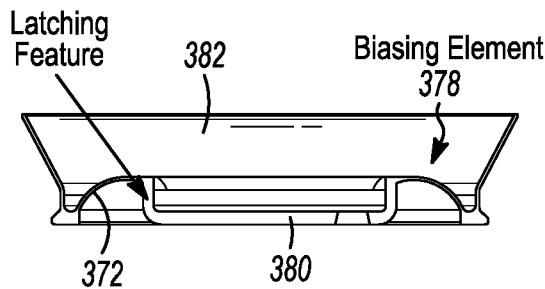
FIG. 17C is a cross-sectional view of the diaphragm of FIGS. 17A-17B.

On inhalation into the nebulizer 210 of FIGS. 14A-C, and 15-16, air flows through vents 294 located in the retainer 216 and into the main chamber 226. When the pressure gradient caused by inhalation is great enough, the duckbill check valve 280 opens outward due to the negative pressure acting on its bottom surface and moves away from the sealing surface 298 of the actuator 222. This allows air to flow into the main chamber 226 of the nebulizer 210 and follow the flow path through the mouthpiece. The negative pressure inside the nebulizer 210 during inhalation also pulls the circumferential exhalation valve 282 down onto the sealing surface 219 of the retainer and prevents inhalation airflow through the exhalation pathway (See FIG. 16). The diameter of the circumferential valve 282 is sufficient such that on inhalation or exhalation it is able to contact the sealing surfaces with no spaces through which air could leak. Referring to FIGS. 15-16, on exhalation, the positive pressure within the nebulizer 210 collapses the duckbill check valve 280 around the sealing surface 298 of the actuator 222, closing the inhalation pathway 297 off from exhalation air flow 299.

Exhalation airflow 299 passes through vents located in the retainer 216, across the circumferential valve 282 and out of the nebulizer 210 through windows located on the retainer 216. The biasing element 278, or the spring, of the diaphragm 220 is located between the actuator latch 260, 262 and the circumferential exhalation valve 282 and is designed to have a resistance to motion that is sufficiently strong enough to hold the actuator 222 in the UP/OFF position until inhalation begins, yet responsive enough to quickly react to negative pressures generated through inhalation. The biasing element 278 may consist of flexible material arranged in a concave-down geometry of that rolls inward in response to negative pressure within the nebulizer 210, acting on the lower surface of the diaphragm 220.

Fourth Embodiment

In a fourth embodiment, as illustrated in FIGS. 17A-17C and 18-21, the exhalation valve 382 is incorporated into the diaphragm 320 as an upwards sloping, circumferential valve of the and acts as a one-way pressure relief valve to pass exhaled air from the nebulizer 310 and prevent air from entering along the exhalation path during inhalation. Inhalation airflow occurs through a one-way flap check valve 380 in the center of the diaphragm 320 that seals on the middle ring 398 of the actuator 320 during exhalation and bends away from the sealing surface of the middle ring 398 during inhalation to permit ambient air to enter the nebulizer 310.

Figure 18:
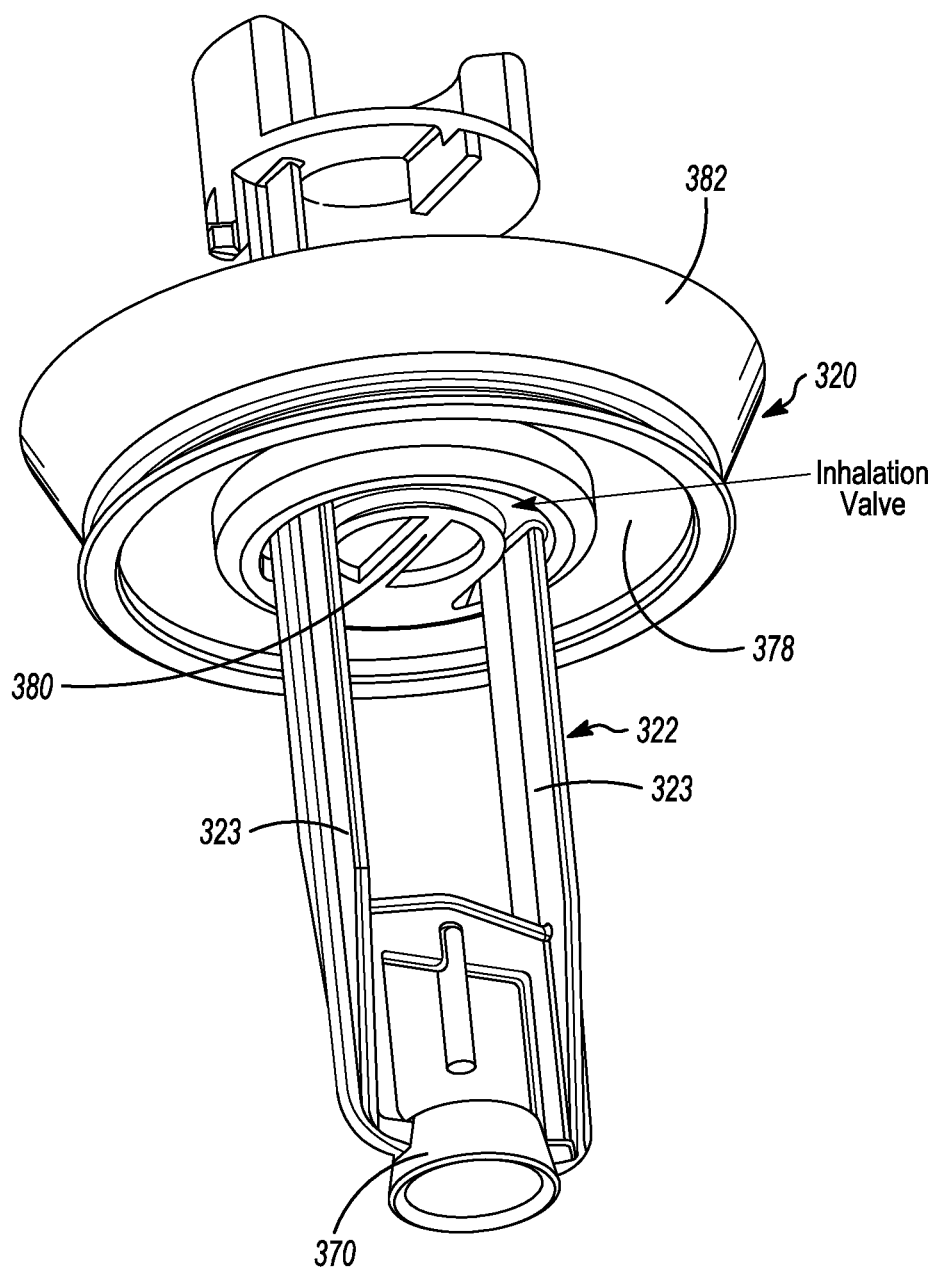
FIG. 18 is a perspective view of an actuator assembled with the diaphragm of FIGS. 17A-17C.
Figure 19:
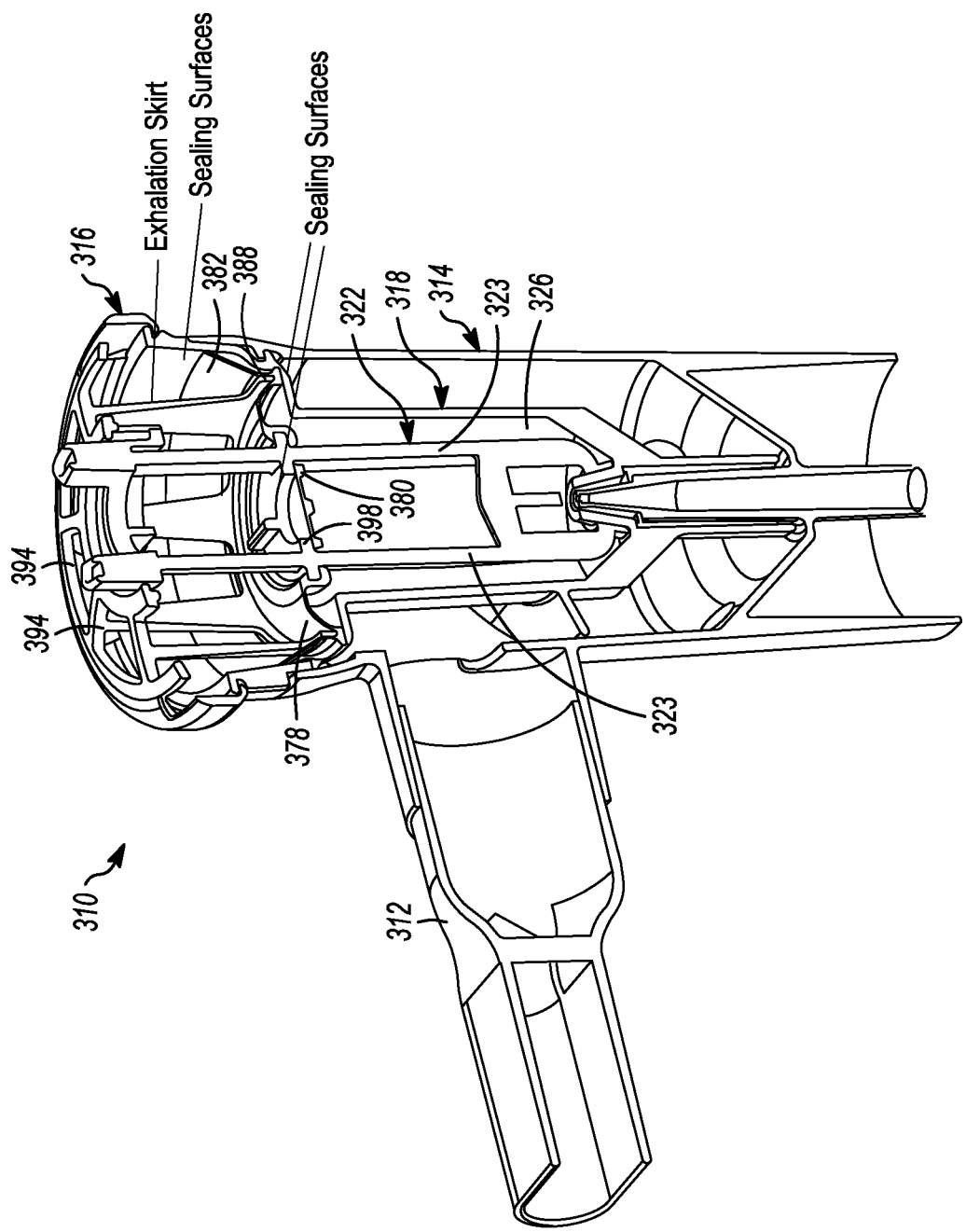
FIG. 19 is a perspective cross-sectional view of the nebulizer of FIG. 1 having the actuator and diaphragm of FIG. 18.

During assembly of this embodiment of nebulizer 310, the actuator 322 may be inserted through the center of the diaphragm 320 from the circumferential exhalation valve 382 side such that the inhalation valve 380 bends out of the way of the tapered positioning flange 370 of the actuator 322 and returns to its unstressed position once the flange 370 is passed. Because a single central actuator shaft, such as illustrated in prior embodiments discussed above, is not available due to the central flap valve configuration of the inhalation valve 380, the actuator 322 is configured with parallel arms 323 and will require limited rotational orientation during assembly. FIG. 18 illustrates the assembled state of the actuator 322 and diaphragm 320 with the inhalation valve 380 in its resting position. The diaphragm 320 is pinned in place between a ring-shaped extrusion 388, also referred to herein as an exhalation skirt, located on the retainer 316 and a sealing surface 389 on the inner housing 318. This configuration isolates the movement of the inhalation valve 380 and biasing element 378 from the circumferential valve 382.

Figure 20:
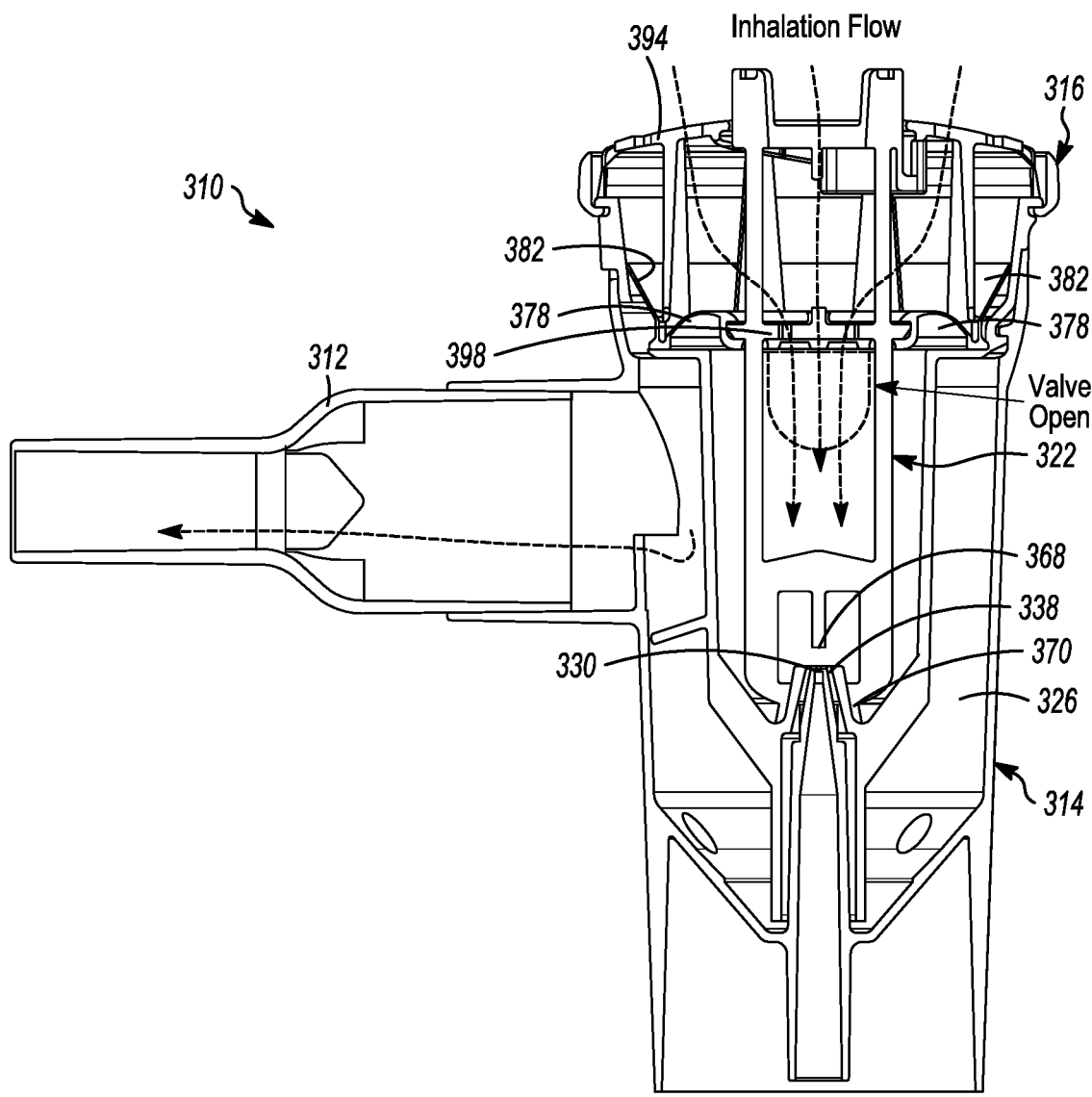
FIG. 20 is a cross-sectional view of the nebulizer of FIG. 19 illustrating an inhalation flow.

Referring to FIG. 20, on inhalation, air flows through vents 394 located in the retainer 316 and into the main chamber 326 of the nebulizer 310. When the pressure gradient caused by inhalation through the mouthpiece 312 is great enough, the exhalation flap forming the inhalation valve 380 hinges away from the sealing surface of the middle ring 398 of the actuator 322 and air flows through the ring 398. This allows air to flow into the main chamber 326 of the nebulizer 310. The negative pressure of the inhalation that opened the inhalation valve 380 also pulls on the bottom of the diaphragm 320, overcoming the bias of the biasing member 378 and the force of the pressurized gas through the gas orifice 330 keeping the actuator 322 in the non-nebulizing position. Pulled by the negative pressure generated by the inhalation through the mouthpiece 312, the actuator 322 moves down into the nebulizer 320 until the diverter 368 is in the nebulizing position.

In the nebulizing position, where the diverter 368 is spaced from the gas orifice 330 and annular fluid orifice 338 at a predetermined distance to cause pressurized gas from the orifice 330 to deflect over the annular orifice 338 and draws up and aerosolizes the medicament into the pressurized gas flow, the nebulized medicament can then mix with the air drawn into the nebulizer. The air drawn into the nebulizer, now laden with aerosolized medicament, can then follow the flow path through the mouthpiece to the patient. The negative pressure inside the nebulizer during inhalation also pulls the circumferential exhalation valve 382 down onto the inner wall of the inner housing 318 forming a sealing surface and preventing inhalation airflow in the exhalation pathway. The diameter of the circumferential exhalation valve 382 on the diaphragm 320 is preferably selected to be sufficient to contact the inner surface of the inner housing 318 on inhalation with no gaps through which air could leak.

Figure 21:
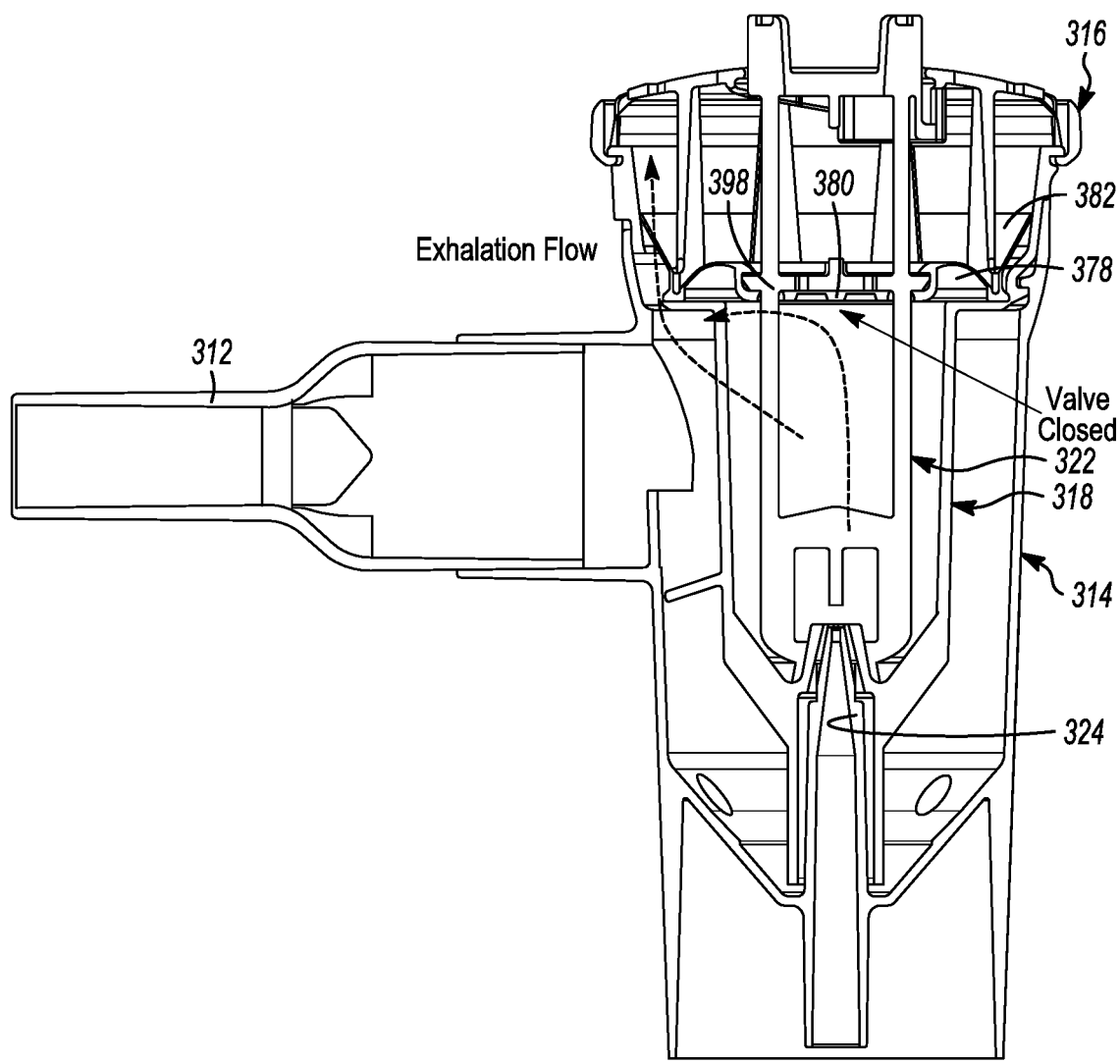
FIG. 21 is a cross-sectional view of the nebulizer of FIG. 19 illustrating an exhalation flow.

Referring to FIG. 21, on exhalation, the positive pressure within the nebulizer 310 returns the inhalation valve 380 to its resting position and pushes it against the sealing surface on the ring 398 of the actuator 322, closing the inhalation pathway off from exhalation air flow. Exhalation airflow passes through vents located in the retainer, across the circumferential valve and out of the nebulizer through windows located on the retainer 316. The diameter of the middle ring of the actuator 322 is sufficient that on exhalation, the inhalation valve 380 completely covers the inhalation orifice defined by the ring 398 of the actuator 322. The biasing element 378, or the spring, of the diaphragm 320 is located between the actuator latch and the outer circumferential exhalation valve 382 and is designed to have a resistance to motion that is sufficiently strong enough to hold the actuator 322 in the UP/OFF position until inhalation begins, yet responsive enough to quickly react to negative pressures generated through inhalation to move the diverter 368 to a nebulizing position. The biasing element 378 may be a flexible material having a concave-down geometry that rolls inward in response to negative pressure within the nebulizer, acting on the lower surface of the diaphragm 320.

Fifth Embodiment

Figure 22:
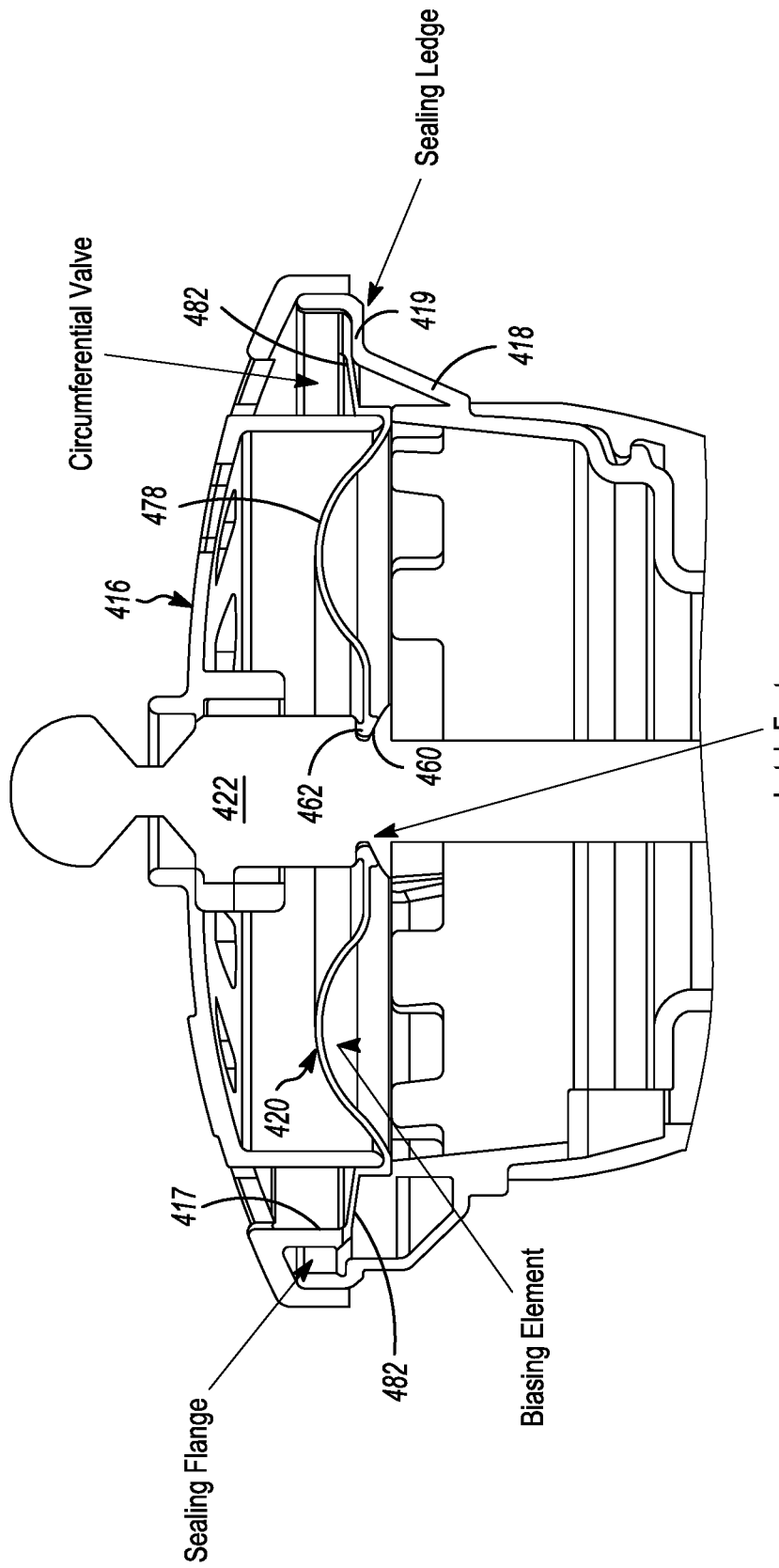
FIG. 22 is a partial cross-sectional view of a nebulizer utilizing a fourth alternative embodiment of the diaphragm of FIG. 3A.
Figure 23:
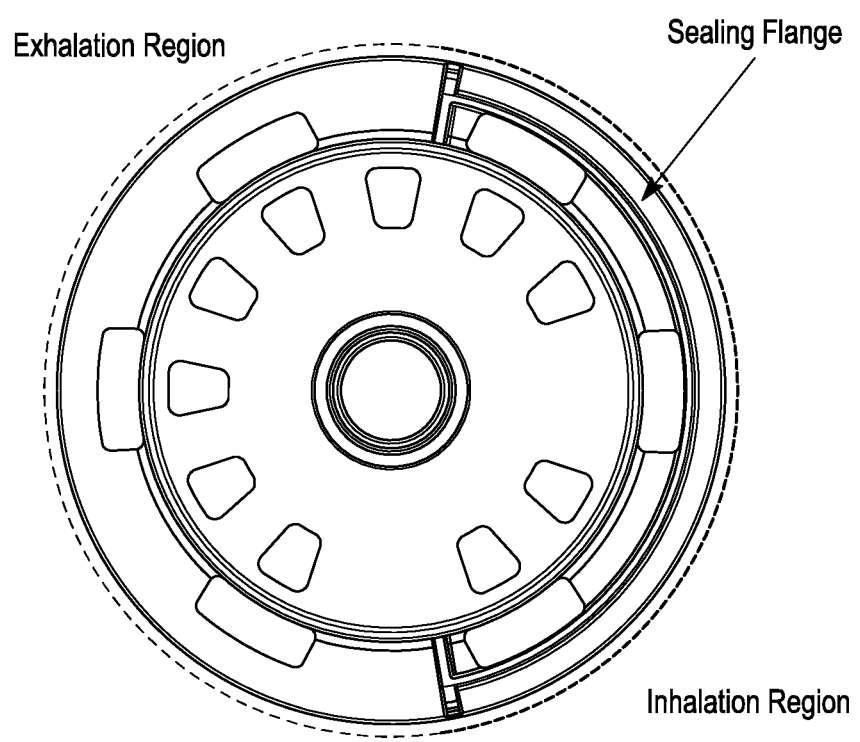
FIG. 23 is a top view of the diaphragm of the nebulizer of FIG. 22

In another embodiment, as illustrated in FIGS. 22-23, the inhalation and exhalation functions may both be incorporated into the circumferential valve 482 of the diaphragm 420 and act as independent one-way pressure relief valves. No airflow occurs between the actuator 422 and diaphragm 420 themselves due to the grommet styled seal created by the actuator latch consisting of a wedge-shaped inner flange 462 in a central opening of the diaphragm 420 and a complementary wedge-shaped groove 460 on an outer circumference of the actuator 422. Separation of inhalation and exhalation airflow pathways is accomplished by a sealing flange 417 incorporated into the retainer 416 that acts as a sealing surface on exhalation and the ledge 419 on the inner housing 418 that acts as a sealing surface on inhalation. The diameter of the circumferential valve 482 on the diaphragm 420 is preferably sufficient to contact the sealing surfaces on both inhalation and exhalation with no spaces through which air could leak.

Figure 24:
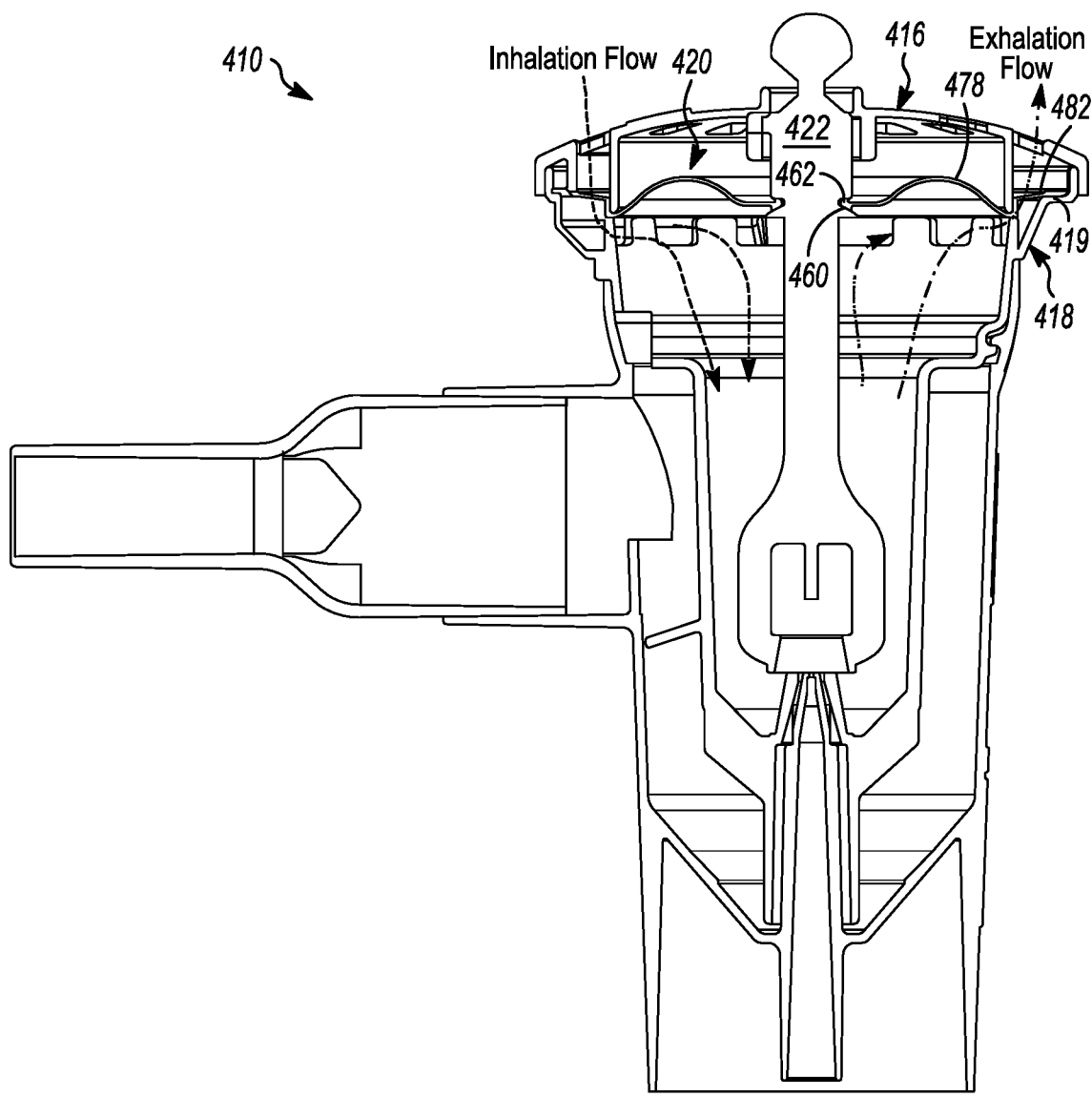
FIG. 24 is a cross-sectional view of a nebulizer incorporating the diaphragm of FIGS. 22-23.

As shown in FIG. 24, windows/vents located in the retainer 416 and inner housing 418 allow expired air to move through the mouthpiece 412, the main nebulizer chamber, across the circumferential valve 482 and out the windows in the exhalation region while ambient air can be drawn through windows in the retainer 416, across the circumferential valve 482 of the diaphragm 420 in the inhalation region and through windows located under the diaphragm, into the body main cavity of the nebulizer. The biasing element 478, or the spring, of the diaphragm 420 is located between the actuator latch 460, 462 and the outer circumferential valve and is designed to have a resistance to motion that is sufficiently strong enough to hold the actuator in the UP/OFF position until inhalation begins, yet responsive enough to quickly react to negative pressures generated through inhalation. The biasing element 478 is comprised of a flexible material in a concave-down geometry that rolls inward in response to negative pressure within the nebulizer 410, acting on the lower surface of the diaphragm 420. The diaphragm 420 is pinned in place between ring shaped extrusions 488, 489 located on the inner housing 418 and retainer 416 and holds the vertical position of the diaphragm constant, in addition to separating the movement of the circumferential valve 482 and the biasing element 478 from each other. The sizing of the semi-circumferential sealing valve and the sealing ledge on the inner housing 418 as well as the separation between the sealing faces and the resting position of the circumferential valve 482 of the diaphragm 420 are determining factors in the flow characteristics of the nebulizer, such as inhalation resistance, exhalation resistance and flow to actuate. In this embodiment, the semi-circumferential sealing valve incorporated into the retainer spans less than half of the circumference of the retainer. Flange thickness and geometry also affect the inhalation and exhalation resistance while the thickness and geometry of the biasing element 478 affect the flow to actuate.

In each of the embodiments presented above, the biasing element worked to lift the actuator and provide a force opposite to the force generated through inhalation. Alternatively, a biasing element that provides a downward force on the actuator could be used. The biasing element would have a resistance to motion that is sufficiently weak enough to allow the actuator to move to the UP/OFF position when pressurized gas is applied through the pressurized gas inlet until inhalation begins, yet responsive enough to quickly react to negative pressures generated through inhalation. Unlike previous configurations, a biasing element working in the opposite direction would hold the actuator down when pressurized gas is not applied to the nebulizer. The biasing element would be comprised of a flexible material that rolls inward in response to negative pressure within the nebulizer, acting on the lower surface of the diaphragm. This solution may be advantageous as it can be used to lower the inhalation flow required to actuate the devices and maximize the duration of aerosol generation over course of a single breath. Though the different variations of diaphragm designs discussed above are presented as separate embodiments, it is to be understood that each inhalation valve, exhalation valve, and biasing element presented may be combined in any configuration of the three elements to the same effect.

The methods by which any of the above-described nebulizers may be manually set to continually nebulize a fluid present in the chamber will now be explained in greater detail. In the currently available nebulizer, the nebulizer has a dial feature that snaps into the retainer and can be rotated. When rotated in a predetermined direction, two (2) finger-like protrusions on the dial push against a ramp profile integrated into the diaphragm and push the diaphragm. This, in turn, lowers the actuator to the nebulizing position and aerosol is produced. In the preferred embodiment, the actuator and dial of the previous generation nebulizer have been merged into a single part, now referred to only as the actuator. Rotation of the actuator, rather than the dial, allows for manual switching between breath actuated and continuous nebulization. In order to accommodate a diaphragm that incorporates the inhalation valve, exhalation valve and biasing element in one part, the ramp profile was incorporated into the retainer in a flange bordering the center opening in the retainer, through which the indicating feature of the actuator protrudes.

Figure 25A:
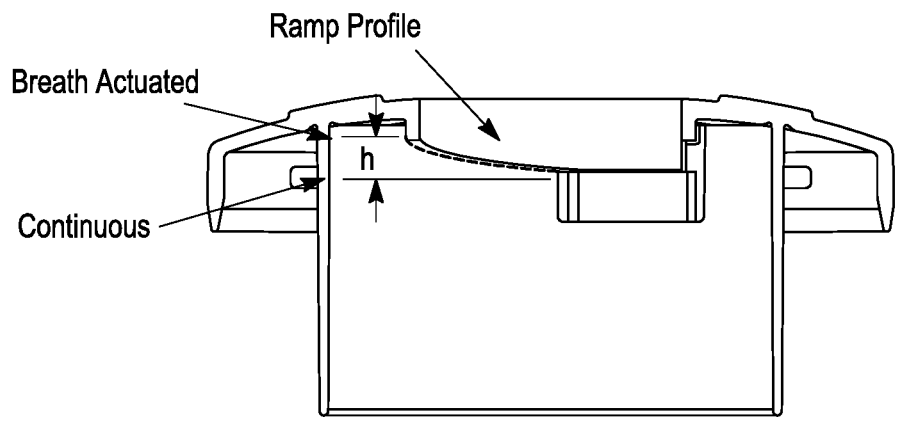
FIG. 25A illustrates a cross-sectional view of a retainer usable in the nebulizer of FIG. 1 and having a ramp profile for use in switching the nebulizer between breath-actuated and continuous nebulization modes
Figure 25B:
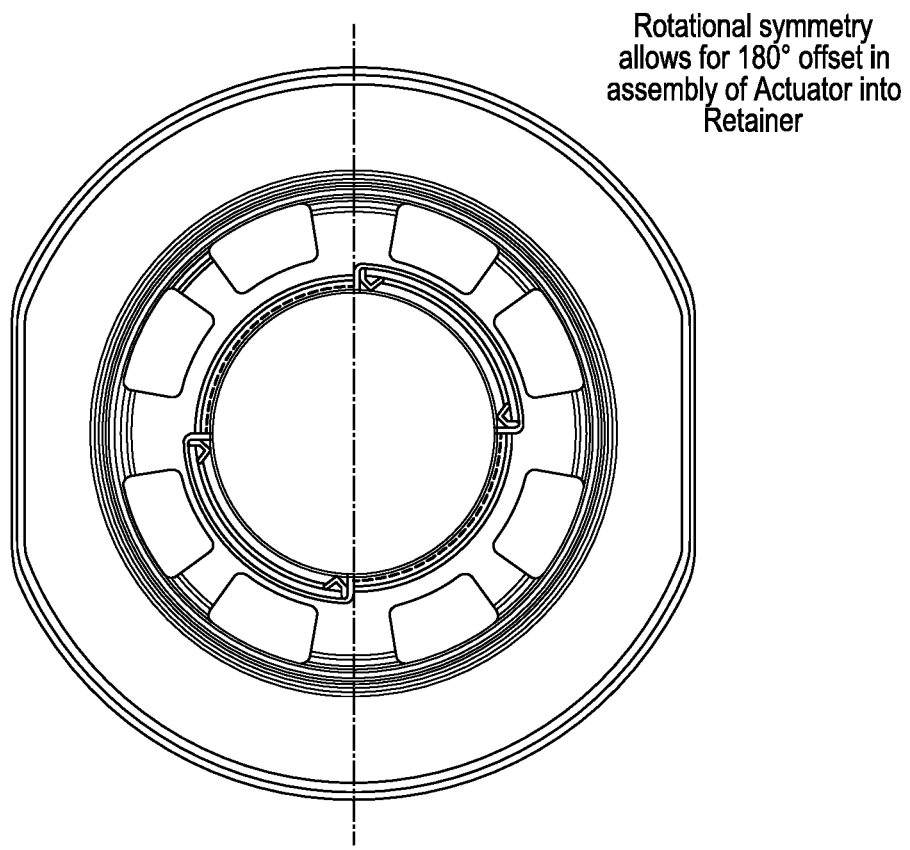
FIG. 25B illustrates a top view of the retainer of FIG. 25A.

FIG. 25 shows one example of how the ramp profile is integrated into the central flange. In this example, the full travel of the ramp occurs over a quarter turn, in other words a rotational angle of approximately 90 degrees. However, this effect can be accomplished over any amount of rotation. Tabs on the actuator follow the profile of the ramp when rotated. The biasing element of the diaphragm, in addition to the force of the pressured gas striking the diverter, push the tabs of the actuator against the ramp flange so that the vertical position, h, of the actuator is determined by where the tabs rest against the ramp. The change in height, h, is such that when the actuator is in its uppermost position, no nebulization occurs while in the lower/continuous position, aerosol is generated. The vertical travel of the ramp is equal to the vertical travel of the actuator in breath-actuated mode on inhalation.

Referring to FIGS. 26A and 26B, the actuator 22 of FIG. 1 is shown in greater detail. The actuator 22 includes a feedback finger located 90 degrees from the tabs of the actuator that protrudes below the indicating surface of the actuator and contains a triangular tip that locks the actuator in the breath actuated mode or continuous mode when the dial ears are rotated. The feedback finger deflects over corresponding detents on the ramp flange and holds the rotational position of the actuator in either mode. The deflection of the feedback finger also provides a haptic indication, or click, to the user when the actuator has been rotated sufficiently to change modes from breath-actuated to continuous nebulization. Due to the limited rotational symmetry of the retainer, the feedback finger is only necessary on one side of the actuator and can be assembled with 180 degree offset, relative to the retainer. Although one specific example of the relative positions of the tabs and feedback finger of the actuator, as well as the dial ears used to rotate the actuator, is shown in FIGS. 26A and B, other configurations and spacings are contemplated.

Figure 27A:
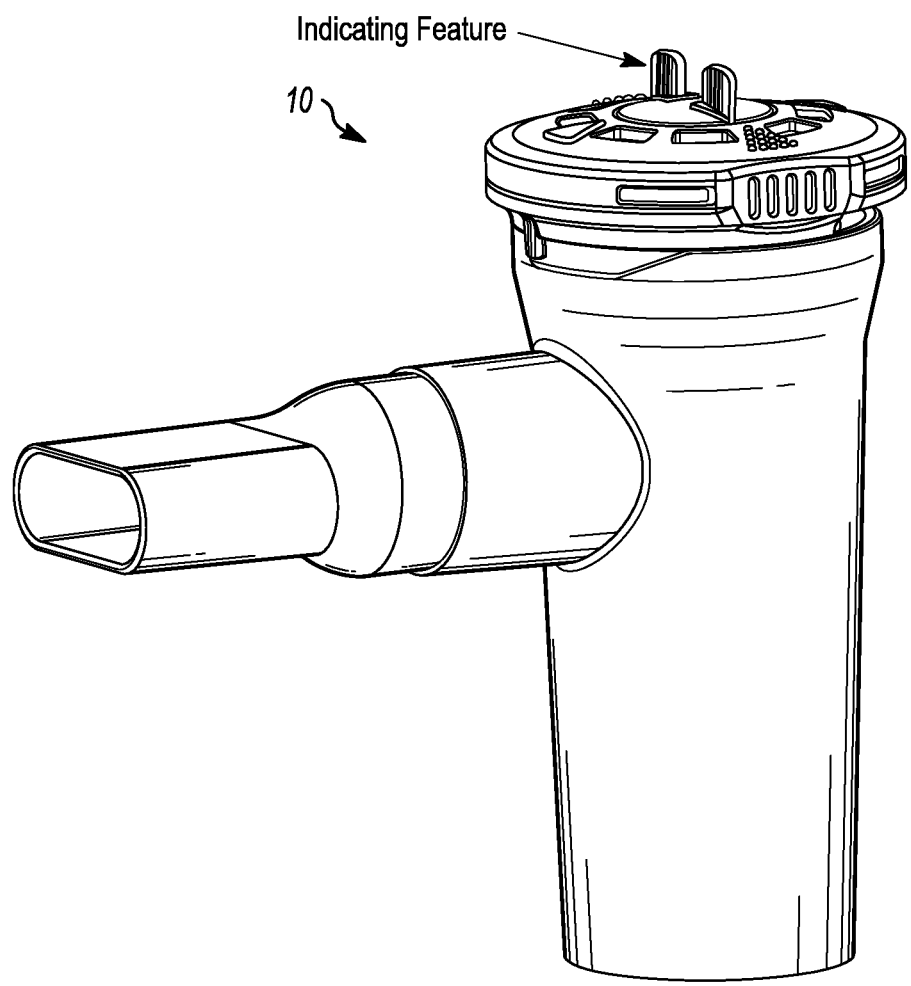
FIG. 27A is a perspective view of the nebulizer of FIG. 1 showing the indicating feature of the actuator in a breath-actuated position.
Figure 27B:
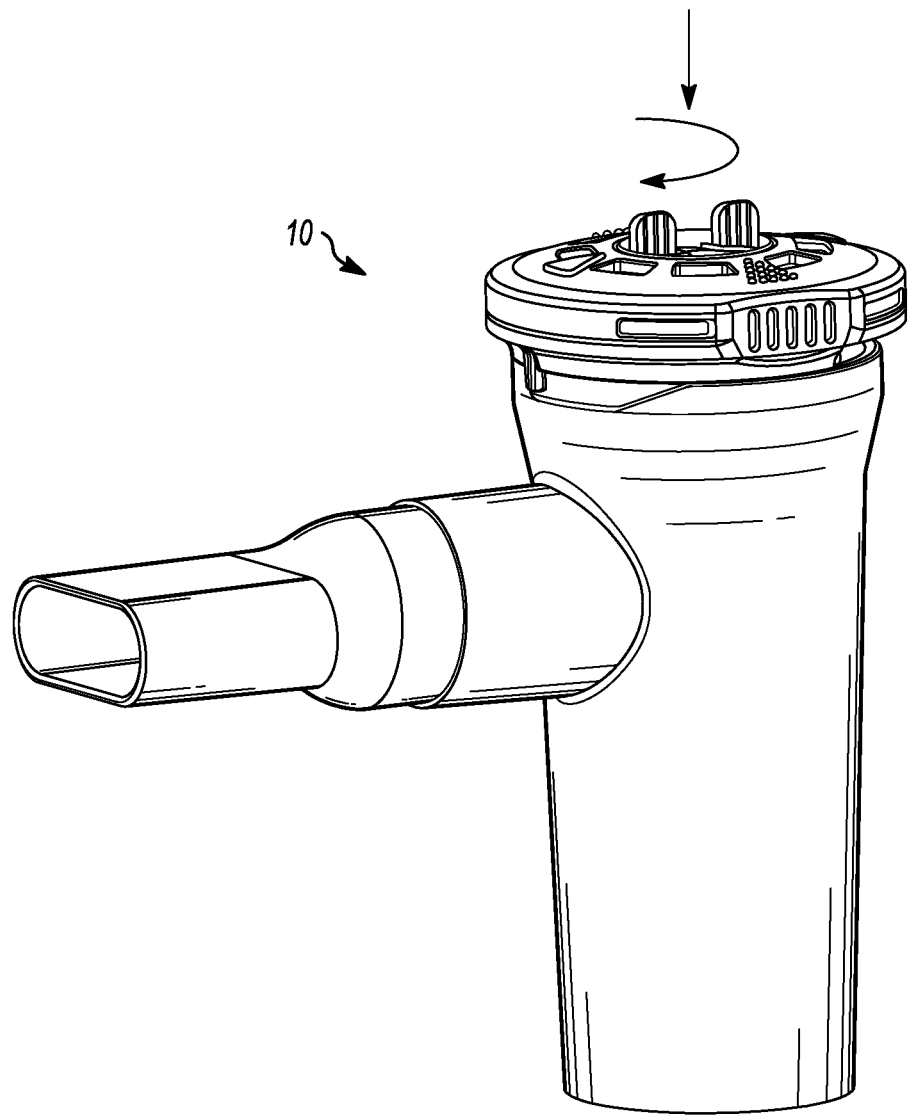
FIG. 27B is the nebulizer of FIG. 27A showing the indicating feature of the actuator in a continuous nebulization position.
Figure 28B:
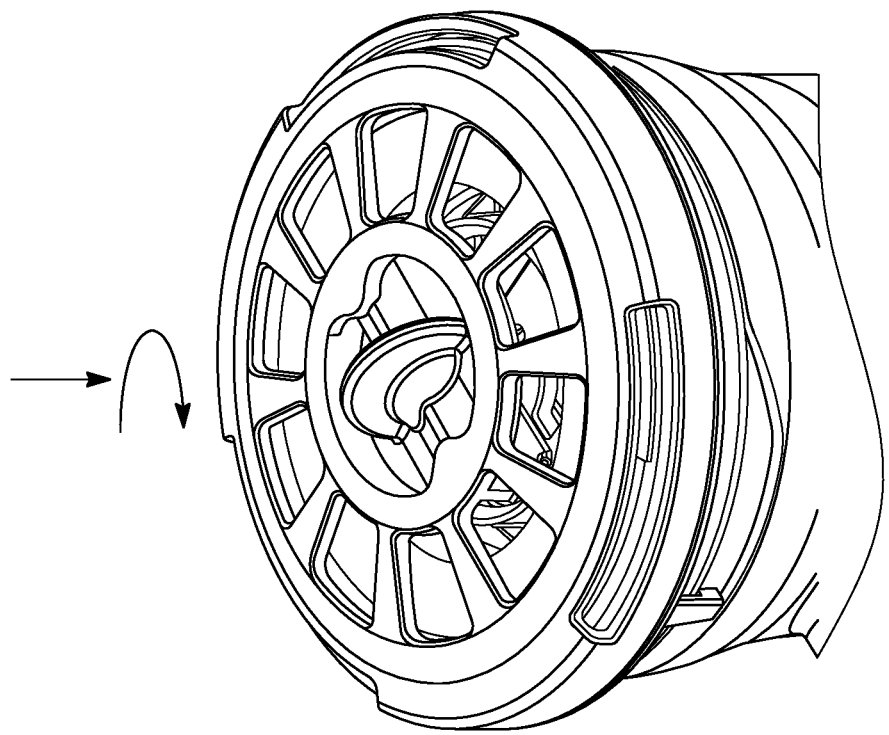
FIGS. 28A-28B illustrate a perspective view of a nebulizer having an alternate embodiment of the indicating feature of FIGS. 27A-27B.
Figure 28A:
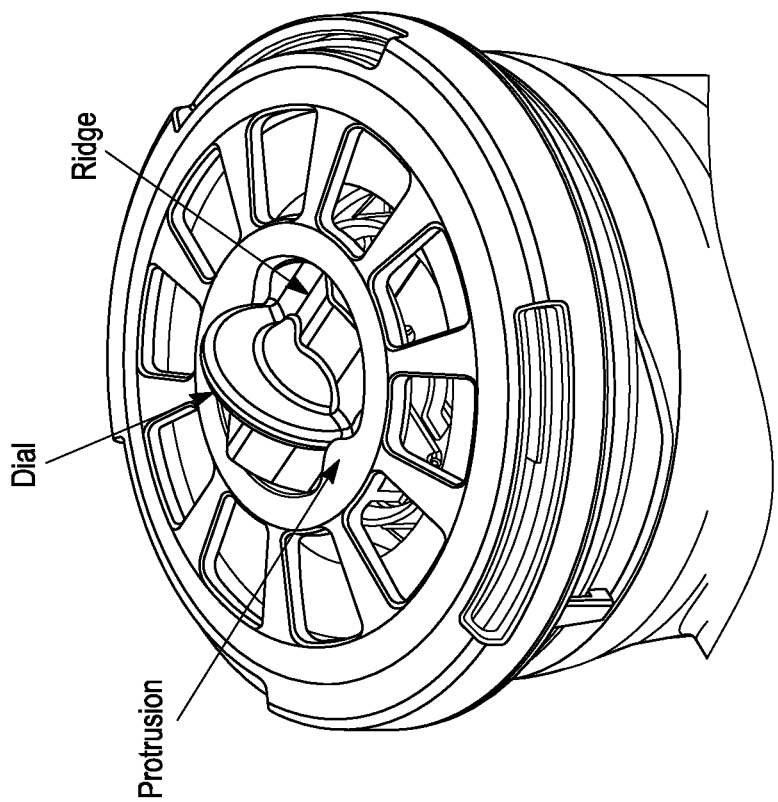
Figure 29:
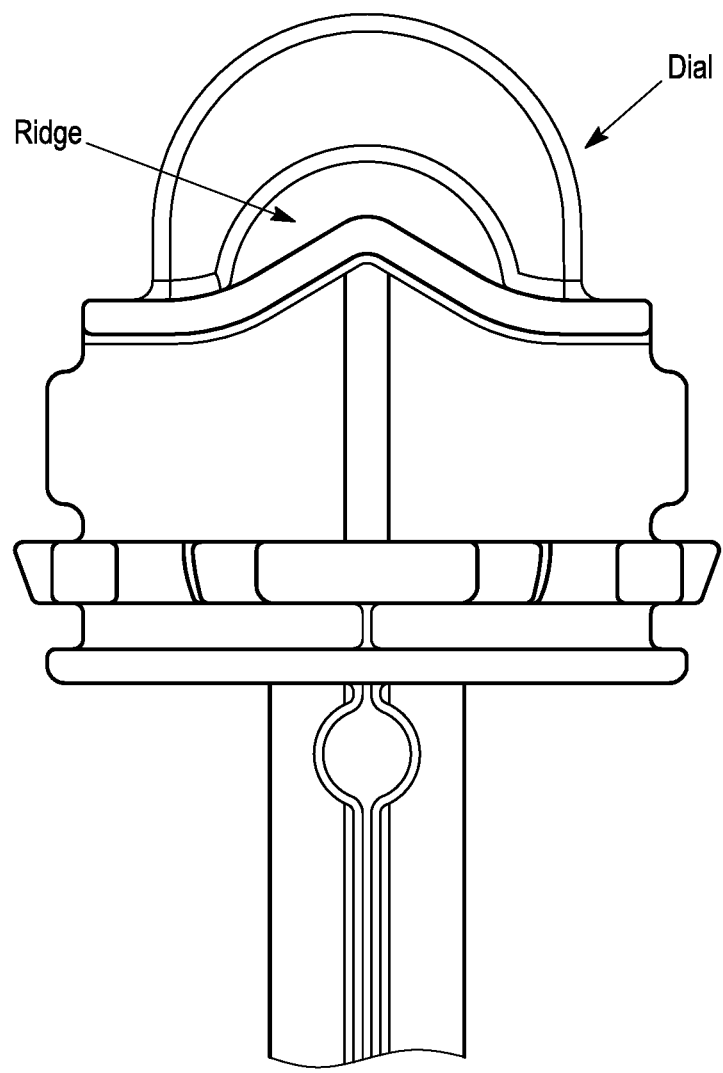
FIG. 29 is a sectional view of the indicating member of FIGS. 28A-28B.
Figure 30:
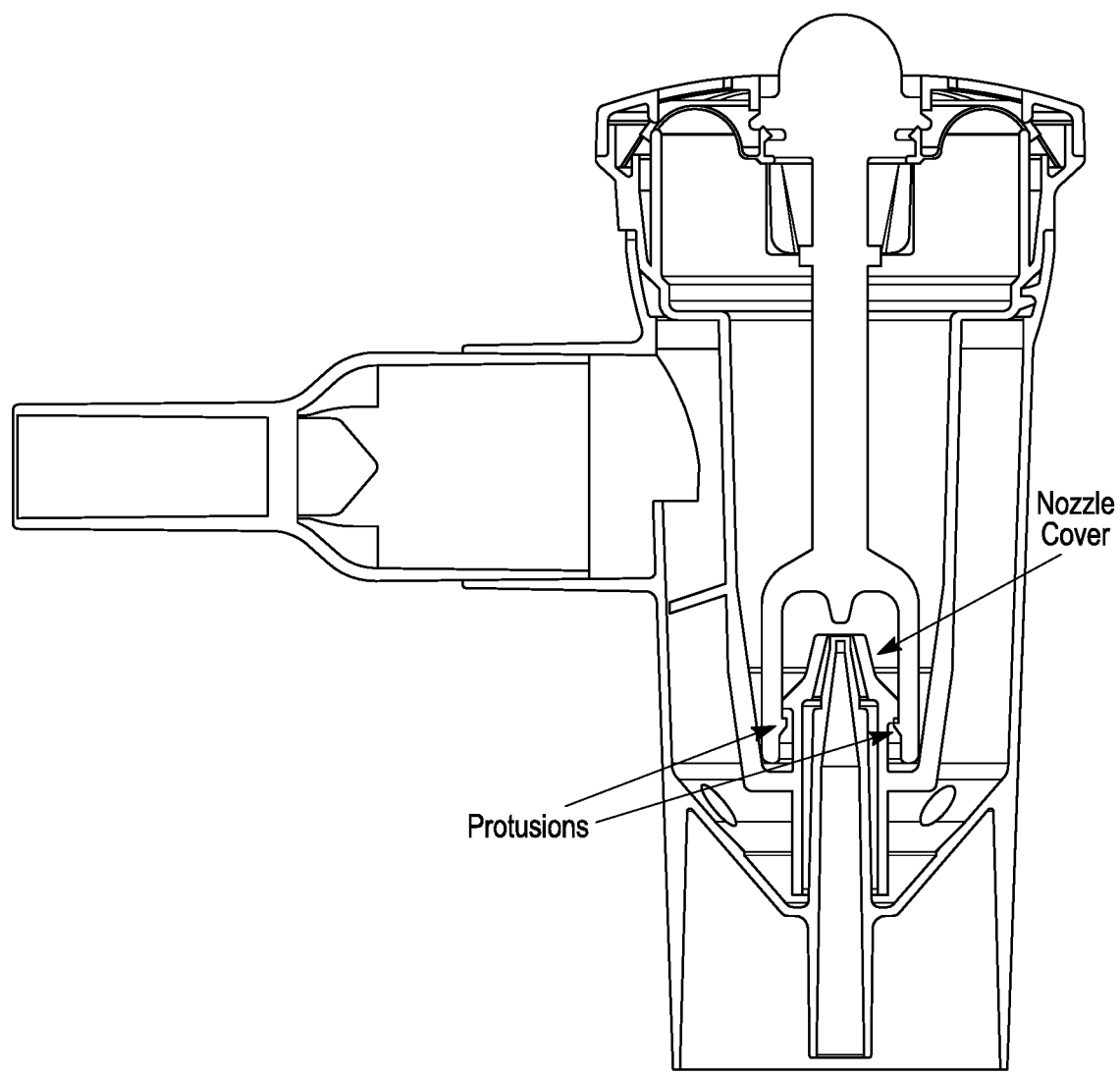
FIG. 30 is a cross-sectional view of a nebulizer incorporating an actuator with the indicating member of FIG. 29.
Figure 31C:
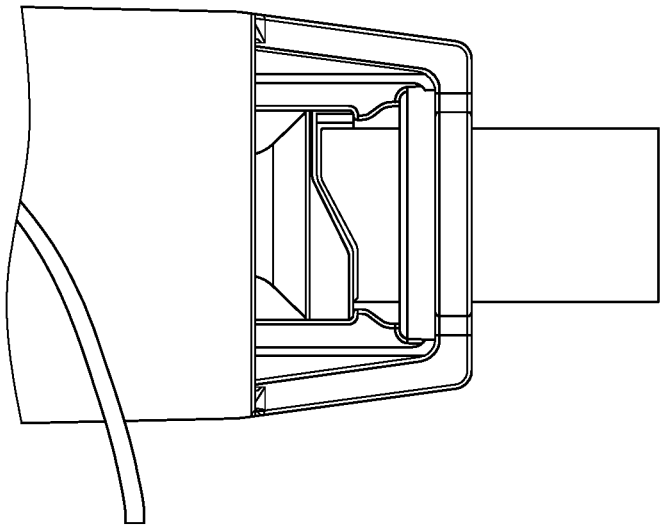
FIGS. 31A-31C illustrate an alternative embodiment of the ramp feature for adjusting an operating mode of FIGS. 25A-25B where the ramp is incorporated into the nozzle cover inside the nebulizer instead of on the retainer on the outside of the nebulizer.
Figure 31B:
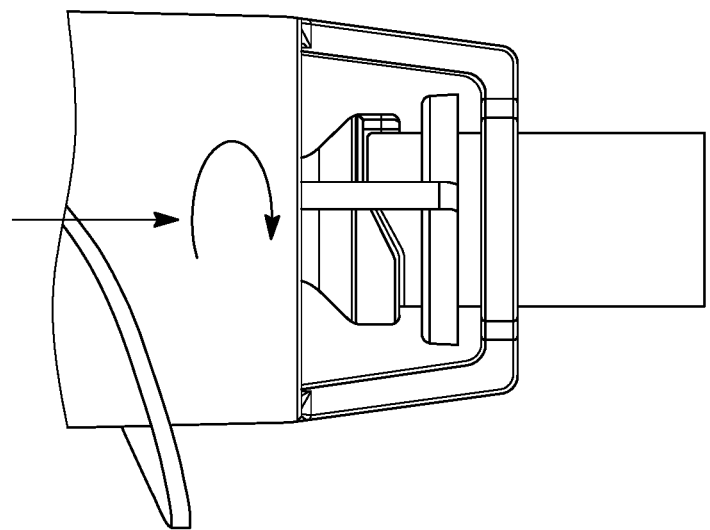
Figure 31A:
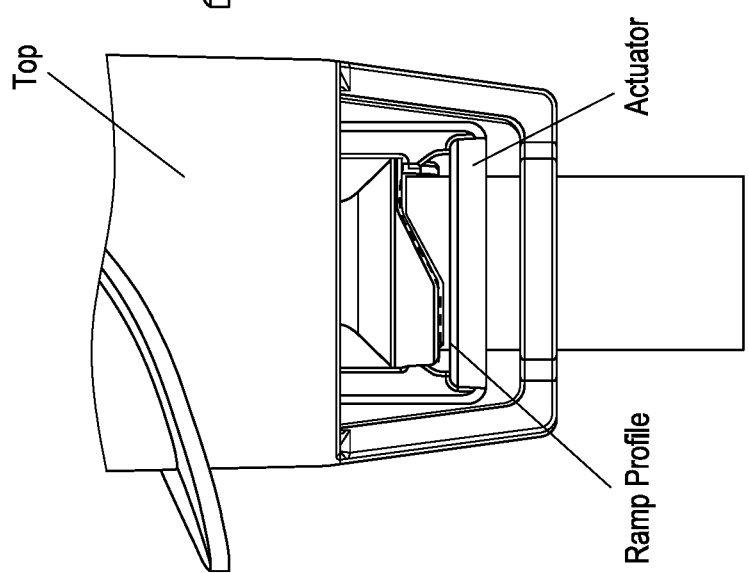

The height that the indicating feature of the actuator extends above the upper surface of the retainer provides a visual indication when nebulization is occurring, as well as the actuator will drop a vertical the mode the nebulizer is set to. On inhalation, distance due to the negative pressure generated inside the nebulizer. When rotated between the breath-actuated and continuous mode, the orientation of the dial ears will change by 90 degrees and the vertical position of the actuator 22 will change, as shown in FIGS. 27A and 27B. The dial ears may also be manually pushed down by the user to generate aerosol.

In one embodiment, the actuator and dial features have again been merged into a single part, now referred to only as the actuator. As before, rotation of the actuator, rather than the dial, allows for switching between breath-actuated nebulization and continuous nebulization. In order to reduce part count and create a design that eases the implementation of automated assembly, the dial was removed and the function incorporated into the actuator and the retainer. In order to switch the nebulizer between continuous nebulization and breath-actuated mode, a method of vertically positioning the actuator, and thus the distance between the baffle surface and the nozzle orifice, is incorporated onto the indicating surface of the actuator with receiving slots integrated into the retainer to hold the actuator in place when in use.

In this embodiment, the surface of the indicating portion of the actuator is designed with a raised ridge with sloping sides. The biasing element of the diaphragm, in addition to the force of the pressurized gas striking the diverter, push the actuator against protrusions found on the retainer and control the vertical positioning of the actuator. When the actuator is rotated such that the ridge move below the protrusions, the actuator is pushed to the down position and the baffle comes into contact with the nozzle jet stream and aerosol is produced. This embodiment allows for rotation in any direction with no radial orientation required on assembly. A flat protrusion from the top of the actuator is included as a feature by which to grip and rotate the actuator. The indicating surface of the actuator may also be manually depressed by pushing down with a finger to move the actuator to the nebulizing position. In another embodiment, the actuator and dial features have again been merged into a single part, now referred to only as the actuator.

As stated previously, rotation of the actuator, rather than the dial, allows for switching between breath-actuated nebulization and continuous nebulization. In order to switch the nebulizer between continuous nebulization and breath-actuated nebulization, a method of vertically positioning the actuator, and thus the distance between the diverter surface and the pressurized gas orifice, is incorporated onto the nozzle cover of the inner housing with protrusions on the actuator that follow the path of the ramp. In this embodiment the outer surface of the nozzle cover incorporates an overhanging ramp profile. The biasing element of the diaphragm, in addition to the force of the pressurized gas striking the diverter, pushes the protrusions located on the lower portion of the actuator against the ramp system and locates the vertical distance of the actuator. During assembly, the actuator snaps over the nozzle cover. A flat protrusion from the top of the actuator is included as a feature by which to grip and rotate the actuator, as in the embodiment of FIGS. 1-11. The indicating surface of the actuator may also be manually depressed by pushing down with a finger to move the actuator to the nebulizing position.

The above embodiments of the nebulizer have been described for use in medical or therapeutic applications. It is noted that the principles of the invention disclosed herein may have applicability to other usages, such as industrial or manufacturing. It is intended that the foregoing detailed description be regarded as illustrative rather than limiting, and that it be understood that the following claims, including all equivalents, are intended to define the scope of this invention.

We claim:

1. A nebulizer comprising:
a housing having a chamber for holding an aerosol;
an inner housing removably insertable into the housing;
an air outlet communicating with the chamber;
a liquid outlet located in the chamber;
a pressurized gas outlet located in the chamber adjacent to the liquid outlet;
an actuator movably disposed along a central axis of the housing, the actuator connected to a diaphragm comprising an inhalation valve, an exhalation valve and a biasing member integrated in a single piece of material;
wherein the biasing member is configured to move a diverter positioned on the actuator between a nebulizing position and a non-nebulizing position with respect to the pressurized gas outlet in response to a patient's breathing;
and wherein the diaphragm defines an inhalation path into the chamber via the inhalation valve when the diverter is in the nebulizing position,
and wherein the exhalation path is defined as being between the inner housing and the housing, separate from the inhalation path, and exhalation occurs through positive pressure via the exhalation valve when the diverter is in the non-nebulizing position.

2. The nebulizer of claim 1, wherein the actuator comprises an attachment region configured to form a friction fit with a portion of a first region of the biasing member in the diaphragm.

3. The nebulizer of claim 2, wherein a second region of the biasing member is held in a fixed position relative to the housing, such that the actuator is movable relative to the housing between the nebulizing position and the non-nebulizing position by the biasing member in response to the patient's breathing.

4. The nebulizer of claim 3, wherein the actuator further comprises a sealing surface, separate from the attachment region, and the inhalation valve of the diaphragm is configured to seal against the sealing surface of the actuator in response to a positive pressure in the chamber and to move away from the sealing surface in response to a negative pressure in the chamber.

5. The nebulizer of claim 4, wherein the biasing member is configured to permit the inhalation valve of the diaphragm to travel with the actuator in response to the patient's breathing.

6. The nebulizer of claim 3, further comprising:
  a lid assembly removably attachable to the housing, wherein the lid assembly includes a diaphragm retention extension;
  wherein when the lid assembly is attached to the housing, the diaphragm is captured between the diaphragm retention extension and a surface of the inner housing.

7. The nebulizer of claim 6, wherein the exhalation valve of the diaphragm is configured to close the exhalation path in response to a negative pressure in the chamber and open the exhalation path in response to a positive pressure in the chamber.

8. The nebulizer of claim 1, wherein:
  the diaphragm is formed in an annular shape;
  the inhalation valve of the diaphragm comprises a center-opening having a valve seat configured to, in response to a positive pressure in the chamber, seal against a sealing surface of the actuator positioned in the diaphragm; and
  the exhalation valve of the diaphragm comprises a outer circumferential portion of the diaphragm configured to seal against an inner circumference of the housing in response to a negative pressure in the chamber.

9. The nebulizer of claim 8, wherein the exhalation valve further comprises a plurality of separate sections of the outer circumferential portion of the diaphragm.

10. The nebulizer of claim 1, wherein the exhalation valve comprises a first section of an outer circumferential portion of the diaphragm and the inhalation valve comprises a second section of the outer circumferential portion of the diaphragm.

11. A nebulizer comprising:
  a housing having a chamber for holding an aerosol;
  an inner housing removably insertable into the housing;
  an air outlet communicating with the chamber;
  a liquid outlet located in the chamber;
  a pressurized gas outlet located in the chamber adjacent to the liquid outlet;
  a diaphragm positioned in the housing, the diaphragm comprising a inhalation valve, an exhalation valve and a biasing member formed in a single piece of material;
  an actuator attached to a central opening of the diaphragm and moveably disposed along an axis parallel to a central axis of the housing, the actuator having a diverter portion positioned at a first end;
  wherein the biasing member is configured to move the diverter portion on the actuator between a nebulizing position and a non-nebulizing position with respect to the pressurized gas outlet in response to a patient's breathing;
  and wherein the diaphragm defines an inhalation path into the chamber via the inhalation valve when the diverter portion is in the nebulizing position,
  and wherein the exhalation path is defined as being between the inner housing and the housing, separate from the inhalation path, and exhalation occurs through positive pressure via the exhalation valve when the diverter portion is in the non-nebulizing position.

12. The nebulizer of claim 11, wherein the actuator comprises an attachment region configured to form a friction fit with a portion of a first region of the biasing member of the diaphragm.

13. The nebulizer of claim 12, wherein a second region of the biasing member is held in a fixed position relative to the housing, such that the actuator is movable relative to the housing between the nebulizing position and the non-nebulizing position by the biasing member in response to the patient's breathing.

14. The nebulizer of claim 13, wherein the actuator further comprises a sealing surface, separate from the attachment region, and the inhalation valve of the diaphragm is configured to seal against the sealing surface of the actuator in response to a positive pressure in the chamber and to move away from the sealing surface in response to a negative pressure in the chamber.

15. The nebulizer of claim 14, wherein the biasing member of the diaphragm is configured to permit the inhalation valve of the diaphragm to travel with the actuator in response to the patient's breathing.

16. The nebulizer of claim 13, further comprising:
  a lid assembly removably attachable to the housing, wherein the lid assembly includes a diaphragm retention extension;
  wherein when the lid assembly is attached to the housing, the diaphragm is captured between the diaphragm retention extension and a surface of the inner housing.

17. The nebulizer of claim 16, and wherein the exhalation valve of the diaphragm is configured to close the exhalation path in response to a negative pressure in the chamber and open the exhalation path in response to a positive pressure in the chamber.

18. The nebulizer of claim 11, further comprising:
  a lid assembly detachably attached to the housing; and
  wherein the actuator further comprises a nebulization state indicator at a second end opposite the first end, the second end extending through the lid assembly, wherein the nebulization state indicator visually indicates one of a nebulizing state or a non-nebulizing state of the nebulizer.

* * * * *

UNITED STATES PATENT AND TRADEMARK OFFICE
CERTIFICATE OF CORRECTION

PATENT NO. : 10,786,638 B2
APPLICATION NO. : 15/644427
DATED : September 29, 2020
INVENTOR(S) : Neritan Alizoti et al.

Page 1 of 1

It is certified that error appears in the above-identified patent and that said Letters Patent is hereby corrected as shown below:

In the Claims

In Column 18, Claim 17, Lines 46, delete "and".

Signed and Sealed this
Twenty-ninth Day of December, 2020

Andrei Iancu
*Director of the United States Patent and Trademark Office*